US008017579B2

(12) United States Patent
Dobson

(10) Patent No.: US 8,017,579 B2

(45) Date of Patent: Sep. 13, 2011

(54) TREATMENT OF VIRAL INFECTIONS

(75) Inventor: Curtis Dobson, Manchester (GB)

(73) Assignee: Ai2 Limited, Manchester (GB)

( * ) Notice: Subject to any disclaimer, the term of this patent is extended or adjusted under 35 U.S.C. 154(b) by 1023 days.

(21) Appl. No.: 10/580,984

(22) PCT Filed: Dec. 20, 2004

(86) PCT No.: PCT/GB2004/005438

§ 371 (c)(1), (2), (4) Date: May 25, 2006

(87) PCT Pub. No.: WO2005/061539

PCT Pub. Date: Jul. 7, 2005

(65) Prior Publication Data

US 2009/0048171 A1 Feb. 19, 2009

(30) Foreign Application Priority Data

Dec. 24, 2003 (GB) .................................. 0329958.3

(51) Int. Cl.
*C07K 7/08* (2006.01)
*A61K 38/10* (2006.01)

(52) U.S. Cl. ............ 514/13; 514/14; 530/326; 530/327; 530/328; 424/9.1

(58) Field of Classification Search .................... 514/13, 514/14; 530/326, 327, 328; 424/9.1
See application file for complete search history.

(56) References Cited

U.S. PATENT DOCUMENTS

| | | | |
|---|---|---|---|
| 7,691,382 | B2 | 4/2010 | Dobson |
| 2002/0164789 | A1 | 11/2002 | Laskowitz et al. |
| 2005/0208078 | A1 | 9/2005 | Hoffman et al. |
| 2005/0266017 | A1 | 12/2005 | Druilhe et al. |
| 2007/0117746 | A1 | 5/2007 | Dobson |
| 2008/0207508 | A1 | 8/2008 | Dobson |
| 2009/0169598 | A1 | 7/2009 | Crutcher |
| 2010/0221273 | A1 | 9/2010 | Dobson |

FOREIGN PATENT DOCUMENTS

| | | |
|---|---|---|
| WO | WO94/04177 | 3/1994 |
| WO | WO98/42751 | * 10/1998 |
| WO | 0215923 | 2/2002 |
| WO | 03026479 | 4/2003 |
| WO | 03052076 | 6/2003 |
| WO | 2005039534 | 5/2005 |
| WO | 2005058959 | 6/2005 |
| WO | 2005082399 | 9/2005 |
| WO | 2007000584 | 1/2007 |

OTHER PUBLICATIONS

Law, et al. "A cross-species comparison of the apolipoprotein B domain that binds to the LDL receptor," Journal of Lipid Research, vol. 31, 1990; 1109-1120.
Azuma et al., A Synthetic Peptide of Human Apoprotein E With Antibacterial Activity, Peptides, (2000), pp. 327-330, 21.
Clay et al., Localization of a Domain in Apolipoprotein E With Both Cytostatic and Cytotoxic Activity, Biochemistry, (1995), pp. 11142-11151, 34.
Owens et al., Apolipoprotein A-I and Its Amphipathic Helix Peptide Analogues Inhibit Human Immunodeficiency Virus-Induced Syncytium Formation, Journal of Clinical Investigations, (Oct. 1990), pp. 1142-1150, 86.
Srinivas et al., Inhibition of Virus-Induced Cell Fusion by Apolipoprotein A-I and Its Amphipathic Peptide Analogs, Journal of Cellular Biochemistry, (1991), pp. 224-237, 45.
Boman, H.G. "Antibacterial peptides: basic facts and emerging concepts," J. Internal Med., 2003: 254: 197-215.
Bradshaw, J.P. "Cationic antimicrobial peptides," Biodrugs 2003: 17 (4): 233-240.
Gait, et al. "Progress in anti-HIV structure-based drug design," TibTech, Oct. 1995 (vol. 13): 430-438.
Hirsch, et al. "Antiretroviral drug resistance testing in adults with HIV infection: Implications for clinical management," JAMA, 1998: 279 (24): 1984-1991.
Olsson, et al. "Possible functional interactions of Apolipoprotein B-100 segments that associate with cell proteoglycans and the ApoB/E receptor," Arteriosclerosis, Thrombosis, and Vascular Biology, vol. 17, No. 1, Jan. 1997; 149-155.
Raffai, et al. "Molecular characterization of two monoclonal antibodies specific for the LDL receptor-binding site of human apolipoprotein E," J. Lipid Research, vol. 36, 1995; 1905-1918.
Wang, et al. "Apolipoprotein E (ApoE) peptide regulates tau phosphorylation via two different signaling pathways," J. Neuroscience Res., 51 (1998): 658-665.
PCT/GB04/05360 ISR dated Oct. 4, 2005.
PCT/GB04/05360 Written Opinion dated Oct. 4, 2005.
PCT/GB04/05360 IPRP dated Jun. 20, 2006.
PCT/GB06/02350 ISR dated Dec. 1, 2006.
PCT/GB06/02350 Written Opinion dated Dec. 1, 2006.
PCT/GB06/02350 IPRP dated Jan. 9, 2008.
PCT/GB05/00769 ISR dated Oct. 18, 2005.
PCT/GB05/00769 Written Opinion dated Oct. 18, 2005.
PCT/GB05/00769 IPRP dated Aug. 30, 2006.
U.S. Appl. No. 10/580,761 Office Action dated Nov. 26, 2008.
U.S. Appl. No. 10/580,761 Office Action dated Jan. 9, 2008.
U.S. Appl. No. 10/580,761 Office Action dated Jun. 9, 2009.
U.S. Appl. No. 10/580,761 Office Action dated Jun. 24, 2008.
U.S. Appl. No. 10/580,761 Notice of Allowance dated Nov. 12, 2009.
U.S. Appl. No. 11/916,627 Office Action dated Dec. 24, 2009.
U.S. Appl. No. 11/916,627 Office Action dated May 10, 2010.
U.S. Appl. No. 11/916,627 Office Action dated Dec. 15, 2010.
U.S. Appl. No. 10/586,416 Office Action dated Dec. 13, 2010.

* cited by examiner

*Primary Examiner* — Chih-Min Kam

(74) *Attorney, Agent, or Firm* — Linda B. Truong; Davis Wright Tremaine LLP

(57) ABSTRACT

The present invention relates to polypeptides, and derivatives or analogues thereof, comprising a tandem repeat of apolipoprotein B, or a truncation thereof, derived from an HSPG receptor binding region of apolipoprotein B. Such peptides are useful for treating or preventing the development of viral infections.

9 Claims, 8 Drawing Sheets

| | Pk No. | Name | Time | Height | Area | Area % |
|---|---|---|---|---|---|---|
| 1 | 1 | | 9.8 | 2.75 | 33.195 | 8 |
| 2 | 2 | | 10.0 | 45.13 | 335.493 | 81 |
| 3 | 3 | | 10.3 | 2.82 | 45.658 | 11 |

SEQUENCE LISTING

<160> NUMBER OF SEQ ID NOS: 48

<210> SEQ ID NO 1
<211> LENGTH: 9
<212> TYPE: PRT
<213> ORGANISM: Homo sapiens

<400> SEQUENCE: 1

Arg Leu Thr Arg Lys Arg Gly Leu Lys
1 5

<210> SEQ ID NO 2
<211> LENGTH: 18
<212> TYPE: PRT
<213> ORGANISM: Homo sapiens

<400> SEQUENCE: 2

Arg Leu Thr Arg Lys Arg Gly Leu Lys Arg Leu Thr Arg Lys Arg Gly
1 5 10 15

Leu Lys

<210> SEQ ID NO 3
<211> LENGTH: 16
<212> TYPE: PRT
<213> ORGANISM: Homo sapiens

<400> SEQUENCE: 3

Arg Thr Arg Lys Arg Gly Arg Lys Arg Thr Arg Lys Arg Gly Arg Lys
1 5 10 15

-continued

```
<210> SEQ ID NO 4
<211> LENGTH: 14
<212> TYPE: PRT
<213> ORGANISM: Homo sapiens

<400> SEQUENCE: 4

Arg Thr Arg Lys Arg Gly Arg Arg Thr Arg Lys Arg Gly Arg
1               5                   10


<210> SEQ ID NO 5
<211> LENGTH: 14
<212> TYPE: PRT
<213> ORGANISM: Homo sapiens

<400> SEQUENCE: 5

Leu Arg Lys Arg Lys Arg Leu Leu Arg Lys Arg Lys Arg Leu
1               5                   10


<210> SEQ ID NO 6
<211> LENGTH: 18
<212> TYPE: PRT
<213> ORGANISM: Homo sapiens

<400> SEQUENCE: 6

Leu Arg Lys Arg Lys Arg Leu Arg Lys Leu Arg Lys Arg Lys Arg Leu
1               5                   10                  15

Arg Lys


<210> SEQ ID NO 7
<211> LENGTH: 18
<212> TYPE: PRT
<213> ORGANISM: Homo sapiens

<400> SEQUENCE: 7

Trp Arg Trp Arg Lys Arg Trp Arg Lys Trp Arg Trp Arg Lys Arg Trp
1               5                   10                  15

Arg Lys


<210> SEQ ID NO 8
<211> LENGTH: 54
<212> TYPE: DNA
<213> ORGANISM: Homo sapiens

<400> SEQUENCE: 8

cgtcttactc gtaaacgtgg tcttaaacgt cttactcgta aacgtggtct taaa           54


<210> SEQ ID NO 9
<211> LENGTH: 54
<212> TYPE: DNA
<213> ORGANISM: Homo sapiens

<400> SEQUENCE: 9

cttcgtactc gtaaacgtgg tcgtaaactt cgtactcgta aacgtggtcg taaa           54


<210> SEQ ID NO 10
<211> LENGTH: 48
<212> TYPE: DNA
<213> ORGANISM: Homo sapiens

<400> SEQUENCE: 10

cgtactcgta aacgtggtcg taaacgtact cgtaaacgtg gtcgtaaa                  48


<210> SEQ ID NO 11
<211> LENGTH: 42
```

<212> TYPE: DNA
<213> ORGANISM: Homo sapiens

<400> SEQUENCE: 11
cgtactcgta aacgtggtcg tcgtactcgt aaacgtggtc gt 42

<210> SEQ ID NO 12
<211> LENGTH: 42
<212> TYPE: DNA
<213> ORGANISM: Homo sapiens

<400> SEQUENCE: 12
cttcgtaaac gtaaacgtct tcttcgtaaa cgtaaacgtc tt 42

<210> SEQ ID NO 13
<211> LENGTH: 54
<212> TYPE: DNA
<213> ORGANISM: Homo sapiens

<400> SEQUENCE: 13
cttcgtaaac gtaaacgtct tcgtaaactt cgtaaacgta aacgtcttcg taaa 54

<210> SEQ ID NO 14
<211> LENGTH: 54
<212> TYPE: DNA
<213> ORGANISM: Homo sapiens

<400> SEQUENCE: 14
tggcgttggc gtaaacgttg gcgtaaatgg cgttggcgta aacgttggcg taaa 54

<210> SEQ ID NO 15
<211> LENGTH: 17
<212> TYPE: PRT
<213> ORGANISM: Homo sapiens

<400> SEQUENCE: 15

Arg Ala Leu Val Asp Thr Leu Lys Phe Val Thr Gln Ala Glu Gly Ala
1 5 10 15

Lys

<210> SEQ ID NO 16
<211> LENGTH: 16
<212> TYPE: PRT
<213> ORGANISM: Homo sapiens

<400> SEQUENCE: 16

Cys Lys Asn Lys Glu Lys Lys Cys Cys Lys Asn Lys Glu Lys Lys Cys
1 5 10 15

<210> SEQ ID NO 17
<211> LENGTH: 18
<212> TYPE: PRT
<213> ORGANISM: Homo sapiens

<400> SEQUENCE: 17

Leu Arg Lys Glu Lys Lys Arg Leu Leu Leu Arg Lys Glu Lys Lys Arg
1 5 10 15

Leu Leu

<210> SEQ ID NO 18
<211> LENGTH: 19
<212> TYPE: PRT
<213> ORGANISM: Homo sapiens

<400> SEQUENCE: 18

Leu Gln Val Ala Glu Arg Leu Thr Arg Lys Tyr Asn Glu Leu Leu Lys
1 5 10 15

Ser Tyr Gln

<210> SEQ ID NO 19
<211> LENGTH: 18
<212> TYPE: PRT
<213> ORGANISM: Homo sapiens

<400> SEQUENCE: 19

Gly Glu Arg Leu Arg Ala Arg Met Glu Gly Glu Arg Leu Arg Ala Arg
1 5 10 15

Met Glu

<210> SEQ ID NO 20
<211> LENGTH: 18
<212> TYPE: PRT
<213> ORGANISM: Homo sapiens

<400> SEQUENCE: 20

Asp Trp Leu Lys Ala Phe Tyr Asp Lys Val Ala Glu Lys Leu Lys Glu
1 5 10 15

Ala Phe

<210> SEQ ID NO 21
<211> LENGTH: 20
<212> TYPE: PRT
<213> ORGANISM: Homo sapiens

<400> SEQUENCE: 21

His Met Leu Asp Val Met Gln Asp His Phe Ser Arg Ala Ser Ser Ile
1 5 10 15

Ile Asp Glu Leu
20

<210> SEQ ID NO 22
<211> LENGTH: 18
<212> TYPE: PRT
<213> ORGANISM: Homo sapiens

<400> SEQUENCE: 22

Arg Asp Ala Asp Asp Leu Gln Lys Arg Arg Asp Ala Asp Asp Leu Gln
1 5 10 15

Lys Arg

<210> SEQ ID NO 23
<211> LENGTH: 18
<212> TYPE: PRT
<213> ORGANISM: Homo sapiens

<400> SEQUENCE: 23

Arg Leu Arg Ala Arg Met Glu Glu Met Arg Leu Arg Ala Arg Met Glu
1 5 10 15

Glu Met

<210> SEQ ID NO 24
<211> LENGTH: 9
<212> TYPE: PRT
<213> ORGANISM: Homo sapiens

<400> SEQUENCE: 24

Leu Arg Lys Leu Arg Lys Arg Leu Leu
1 5

<210> SEQ ID NO 25
<211> LENGTH: 22
<212> TYPE: PRT
<213> ORGANISM: Homo sapiens

<400> SEQUENCE: 25

Pro Tyr Leu Asp Asp Phe Gln Lys Lys Trp Gln Glu Glu Met Glu Leu
1 5 10 15

Tyr Arg Gln Lys Val Glu
20

<210> SEQ ID NO 26
<211> LENGTH: 22
<212> TYPE: PRT
<213> ORGANISM: Homo sapiens

<400> SEQUENCE: 26

Pro Leu Gly Glu Glu Met Arg Asp Arg Ala Arg Ala His Val Asp Ala
1 5 10 15

Leu Arg Thr His Leu Ala
20

<210> SEQ ID NO 27
<211> LENGTH: 22
<212> TYPE: PRT
<213> ORGANISM: Homo sapiens

<400> SEQUENCE: 27

Pro Tyr Ser Asp Glu Leu Arg Gln Arg Leu Ala Ala Arg Leu Glu Ala
1 5 10 15

Leu Lys Glu Asn Gly Gly
20

<210> SEQ ID NO 28
<211> LENGTH: 22
<212> TYPE: PRT
<213> ORGANISM: Homo sapiens

<400> SEQUENCE: 28

Ala Arg Leu Ala Glu Tyr His Ala Lys Ala Thr Glu His Leu Ser Thr
1 5 10 15

Leu Ser Glu Lys Ala Lys
20

<210> SEQ ID NO 29
<211> LENGTH: 22
<212> TYPE: PRT
<213> ORGANISM: Homo sapiens

<400> SEQUENCE: 29

Pro Val Leu Asp Glu Phe Arg Glu Lys Leu Asn Glu Glu Leu Glu Ala
1 5 10 15

Leu Lys Gln Lys Met Lys
20

<210> SEQ ID NO 30
<211> LENGTH: 18
<212> TYPE: PRT
<213> ORGANISM: Homo sapiens

<400> SEQUENCE: 30

Val Thr Asp Tyr Gly Lys Asp Leu Met Glu Lys Val Lys Ser Pro Glu
1 5 10 15

Leu Gln

<210> SEQ ID NO 31
<211> LENGTH: 18
<212> TYPE: PRT
<213> ORGANISM: Homo sapiens

<400> SEQUENCE: 31

Val Thr Asp Tyr Gly Lys Asp Leu Met Glu Lys Val Lys Glu Trp Leu
1 5 10 15

Asn Ser

<210> SEQ ID NO 32
<211> LENGTH: 18
<212> TYPE: PRT
<213> ORGANISM: Homo sapiens

<400> SEQUENCE: 32

Asn Phe His Ala Met Phe Gln Pro Phe Leu Glu Met Ile His Glu Ala
1 5 10 15

Gln Gln

<210> SEQ ID NO 33
<211> LENGTH: 16
<212> TYPE: PRT
<213> ORGANISM: Homo sapiens

<400> SEQUENCE: 33

Lys Phe Met Glu Thr Val Ala Glu Lys Ala Leu Gln Glu Tyr Arg Lys
1 5 10 15

<210> SEQ ID NO 34
<211> LENGTH: 18
<212> TYPE: PRT
<213> ORGANISM: Homo sapiens

<400> SEQUENCE: 34

Arg Arg Trp Arg Lys Arg Trp Arg Lys Trp Arg Trp Arg Lys Arg Trp
1 5 10 15

Arg Lys

<210> SEQ ID NO 35
<211> LENGTH: 18
<212> TYPE: PRT
<213> ORGANISM: Homo sapiens

<400> SEQUENCE: 35

Lys Arg Trp Arg Lys Arg Trp Arg Lys Trp Arg Trp Arg Lys Arg Trp
1 5 10 15

Arg Lys

<210> SEQ ID NO 36
<211> LENGTH: 18
<212> TYPE: PRT
<213> ORGANISM: Homo sapiens

<400> SEQUENCE: 36

Leu Arg Trp Arg Lys Arg Trp Arg Lys Trp Arg Trp Arg Lys Arg Trp
1 5 10 15

Arg Lys

<210> SEQ ID NO 37
<211> LENGTH: 18
<212> TYPE: PRT
<213> ORGANISM: Homo sapiens

<400> SEQUENCE: 37

His Arg Trp Arg Lys Arg Trp Arg Lys Trp Arg Trp Arg Lys Arg Trp
1               5                   10                  15

Arg Lys

<210> SEQ ID NO 38
<211> LENGTH: 17
<212> TYPE: PRT
<213> ORGANISM: Homo sapiens

<400> SEQUENCE: 38

Arg Trp Arg Lys Arg Trp Arg Lys Trp Arg Trp Arg Lys Arg Trp Arg
1               5                   10                  15

Lys

<210> SEQ ID NO 39
<211> LENGTH: 18
<212> TYPE: PRT
<213> ORGANISM: Homo sapiens

<400> SEQUENCE: 39

Arg Arg Trp Arg Lys Arg Trp Arg Lys Arg Arg Trp Arg Lys Arg Trp
1               5                   10                  15

Arg Lys

<210> SEQ ID NO 40
<211> LENGTH: 18
<212> TYPE: PRT
<213> ORGANISM: Homo sapiens

<400> SEQUENCE: 40

Lys Arg Trp Arg Lys Arg Trp Arg Lys Lys Arg Trp Arg Lys Arg Trp
1               5                   10                  15

Arg Lys

<210> SEQ ID NO 41
<211> LENGTH: 18
<212> TYPE: PRT
<213> ORGANISM: Homo sapiens

<400> SEQUENCE: 41

Leu Arg Trp Arg Lys Arg Trp Arg Lys Leu Arg Trp Arg Lys Arg Trp
1               5                   10                  15

Arg Lys

<210> SEQ ID NO 42
<211> LENGTH: 18
<212> TYPE: PRT
<213> ORGANISM: Homo sapiens

<400> SEQUENCE: 42

His Arg Trp Arg Lys Arg Trp Arg Lys His Arg Trp Arg Lys Arg Trp
1               5                   10                  15

Arg Lys

<210> SEQ ID NO 43
<211> LENGTH: 16
<212> TYPE: PRT
<213> ORGANISM: Homo sapiens

<400> SEQUENCE: 43

Arg Trp Arg Lys Arg Trp Arg Lys Arg Trp Arg Lys Arg Trp Arg Lys
1 5 10 15

<210> SEQ ID NO 44
<211> LENGTH: 16
<212> TYPE: PRT
<213> ORGANISM: Homo sapiens

<400> SEQUENCE: 44

Arg Trp Arg Lys Arg Gly Arg Lys Arg Trp Arg Lys Arg Gly Arg Lys
1 5 10 15

<210> SEQ ID NO 45
<211> LENGTH: 16
<212> TYPE: PRT
<213> ORGANISM: Homo sapiens

<400> SEQUENCE: 45

Arg Thr Arg Lys Arg Trp Arg Lys Arg Thr Arg Lys Arg Gly Arg Lys
1 5 10 15

<210> SEQ ID NO 46
<211> LENGTH: 16
<212> TYPE: PRT
<213> ORGANISM: Homo sapiens

<400> SEQUENCE: 46

Arg Trp Arg Lys Arg Trp Arg Lys Arg Trp Arg Lys Arg Trp Arg Lys
1 5 10 15

<210> SEQ ID NO 47
<211> LENGTH: 18
<212> TYPE: PRT
<213> ORGANISM: Homo sapiens

<400> SEQUENCE: 47

Arg Trp Arg Lys Arg Trp Arg Trp Arg Lys Arg Trp Arg Trp Arg Lys
1 5 10 15

Arg Trp

<210> SEQ ID NO 48
<211> LENGTH: 18
<212> TYPE: PRT
<213> ORGANISM: Homo sapiens

<400> SEQUENCE: 48

Leu Arg Thr Arg Lys Arg Gly Arg Lys Leu Arg Thr Arg Lys Arg Gly
1 5 10 15

Arg Lys

TREATMENT OF VIRAL INFECTIONS

This application is the National Phase of International Application PCT/GB2004/005438, filed Dec. 20, 2004, which designated the U.S. and that International Application was published under PCT Article 21(2) in English. This application also includes a claim of priority under 35 U.S.C. §119 (a) and §365(b) to British patent application No. GB0329958.3, filed Dec. 24, 2003.

The present invention relates to polypeptides, derivatives or analogues thereof, and to nucleic acids encoding the same with anti-viral activity. The invention further provides the use of such polypeptides, derivatives, analogues or nucleic acids as medicaments, and also in methods of treatment.

Antiviral agents may target one of six stages of the viral replication cycle, these being:

1. Attachment of the virus to the cell;
2. Penetration (or fusion of the viral membrane with the cell membrane);
3. Uncoating of the virus;
4. Replication of the viral nucleic acids;
5. Maturation of progeny virus particles; and
6. Release of progeny virus into extracellular fluids.

Of these six stages, replication (stage 4 above) is the target, which is most effectively influenced by conventional antiviral therapies. Attachment of the virus to the cell (stage 1 above) is however arguably a more attractive target, as the agent does not need to pass into the host cell. However, this remains an area where few successful therapies have been developed.

It is therefore one object of the present invention to provide therapeutic agents that modulate viral activity including entry and attachment to cells.

Lipoproteins (LPs) are globular macromolecular complexes present in serum and other extracellular fluids, consisting of lipid and protein, and are involved in the transport of lipid around the body. They have been categorised according to their density, with the main classes being high density lipoprotein (HDL), low density lipoprotein (LDL), and very low density lipoprotein (VLDL). Their proteins are referred to as apolipoproteins, and a number of these have been described, including apolipoproteins A, B, C, D, E, F, G, H, and J. In addition, several sub-types of apolipoproteins A, B and C have been documented.

Various interactions have been described linking LPs with viruses. These mostly involving binding of viruses to lipoproteins, with this resulting in either diminished viral infectivity, or conversely providing a 'hitchhiker' method for the virus to enter cells. Additionally, several viruses make use of cellular receptors for LPs (e.g. the LDL receptor) as a means of entering cells, although these receptors can also be released by cells as endogenous antiviral agents (for example a soluble form of the VLDL receptor is released into culture medium by HeLa cells and inhibits human rhinovirus infection). Furthermore, direct binding between certain apolipoproteins and viral proteins has also been reported. For example:

a. Hepatitis C virus core protein binds to apolipoprotein AII;
b. Hepatitis B virus surface antigen binds apolipoprotein H; and
c. Simian immunodeficiency virus (SIV) gp32 protein, and human immunodeficiency virus (HIV) gp41 protein binds to apolipoprotein A1.

Work conducted in the laboratory of the inventor has shown that the presence of latent herpes simplex virus type 1 (HSV1) in brain and the possession of a particular allele of a specific gene, the APOE-e4 allele of the APOE gene, increases the risk of development of Alzheimer's disease (AD). Taken with the additional finding that APOE-e4 carriers are more likely to suffer from cold sores (which are lesions found after reactivation of HSV1 in the peripheral nervous system), these results suggested that APOE-e4 carriers are more likely to suffer damage from HSV1 infections, and suggests that there may be interactions between apolipoprotein E and certain viruses (although such interactions need not necessarily involve antiviral effects).

Apolipoprotein E has been shown to have effects on the immune system (seemingly unrelated to its role in lipid metabolism) including suppression of T lymphocyte proliferation. Interactions between a number of peptides derived from residues 130-169 of apoE with lymphocytes have been examined (Clay et al., Biochemistry, 34: 11142-11151 (1995)). The region consisting of apoE residues 141-149 are predicted to be particularly important. Similar interactions of such peptides have been described in neuronal cell lines.

WO 94/04177 discloses that administration of particles containing lipid and amphipathic helical peptides allows clearance of toxins produced by micro-organisms, and may increase the effectiveness of antibacterial drugs via an effect on bacterial membranes. However, there is no suggestion that such apoA-derived peptide containing particles may be used as antiviral medicines. It is also not clear whether administration of the peptides in particles, which is a key component of the disclosed development (whether the particles are formed before administration or endogenously), would result in effective utilisation of any antiviral action of either component of the particle.

An amphipathic helical peptide derived from apoA (described by Ananatharamiah in Meth. Enz., 128: 627-647 (1986)) has been shown to prevent fusion of viral membranes with cell membranes, and furthermore prevent the fusion of membranes of infected cells (Srinivas et al. J. Cellular Biochem., 45: 224-237 (1991)). The peptide was also effective at preventing fusion for both HSV1 and HIV (Owens et al., J. Clin. Invest., 86: 1142-1150 (1990)). However, the peptide had no effect at all on attachment of HSV1 at least to cells (Srinivas et al. supra).

Azuma et al. have reported that peptide derivatives of apoe have a strong antibacterial action, comparable with that of gentamicin (Peptides, 21: 327-330 (2000)). ApoE 133-162 was the most effective, with apoE 134-155 having little effect.

In the light of the research described above, the inventor decided to conduct experiments to investigate the antiviral activity of polypeptides from a range of different apolipoproteins and derivatives thereof.

According to a first aspect of the present invention, there is provided a polypeptide, derivative or analogue thereof, comprising a tandem repeat of apolipoprotein B or a truncation thereof, characterised in that the tandem repeat or truncation thereof is derived from an HSPG receptor binding region of apolipoprotein B.

It is preferred that the peptide according to the first aspect of the invention comprises a tandem repeat which is derived from an apolipoprotein B LDL receptor binding domain cluster B, as defined by Law and Scott (J Lipid Res. 1990; 31:1109-20) which may be located within the HSPG receptor binding region of apolipoprotein B.

By "derivative or analogue thereof" we mean a polypeptide within which amino acids residues are replaced by residues (whether natural amino acids, non-natural amino acids or amino acid mimics) with similar side chains or peptide backbone properties. Additionally, the terminals of such peptides may be protected by N and C-terminal protecting groups with similar properties to acetyl or amide groups.

By "a truncation thereof" we mean that the tandem repeat is reduced in size by removal of amino acids. The reduction of amino acids may be by removal of residues from the C or N terminal of the peptide or may be by deletion of one or more amino acids from within the core of the peptide.

The term "derived from" as used herein is intended to describe or include a tandem repeat, which is a derivative or a modification of an amino sequence forming the HSPG receptor binding region of apolipoprotein B, or the apolipoprotein B LDL receptor binding domain cluster B therein. Surprisingly, polypeptides, derivatives or analogues thereof according to the first aspect of the invention have been shown to exhibit antiviral activity.

The inventor decided to investigate the antiviral activity of tandem repeats from apolipoproteins when he realised that some peptides derived from a heparan sulphate proteoglycan (HSPG)/LDL receptor binding region of apolipoprotein E show some antiviral activity (e.g. a tandom repeat of $apoE_{141-149}$). The inventor therefore examined whether heparin binding regions from a number of other apolipoproteins showed any antiviral activity. He examined, amongst others, the following:—

(i) A heparin binding region within apolipoprotein B ($ApoB_{1000-1016}$ having amino acid sequence RALVDTLKFVTQAEGAK), referred to herein as GIN 17 (SEQ ID No.15). GIN 17 is not linked to LDLR interactions (Shih et al. 1990 PNAS). As this was a 17-mer, a tandem repeat of GIN 17 was not constructed;

(ii) A peptide referred to herein as GIN 16 (SEQ ID No. 48), which is a slightly modified form of a tandem repeat peptide of the LDLR receptor binding region B of apolipoprotein B, and constructed by the inventor. GIN 16 consists of a human apolipoprotein $B_{(3359-3367)\ repeat}$ having amino acid sequence LRTRKRGRKLRTRKRGRK, in which residues 3359 and 3360 are reversed, and the leucine residue at position 3366 is replaced with an arginine;

(iii) A heparin binding region within apolipoprotein H, referred to herein as GIN 27 (SEQ ID No.16). GIN 27 is a tandem repeat peptide, $ApoH_{(281-288)\ repeat}$ having amino acid sequence CKNKEKKCCKNKEKKC, constructed by the inventor based on the heparin binding region of apolipoprotein H (aka beta2 glycoprotein) Guerin et al. J Biol. Chem. 2002 Jan. 25; 277(4):2644-9.

In addition, the inventor examined a range of cationic amphipathic alpha helices derived from a number of human apolipoproteins for antiviral activity. For example, they investigated:—

(i) GIN 28 (SEQ ID No. 17) (LRKEKKRLLLRKEKKRLL), which is a form of GIN 27 referred to above, which has been modified by the inventor, in which the positively charged lysine residues have been left in place, but some of the features of $ApoE_{141-149}$ (the apoE derived peptide—see Example 1) have been added (notably an initiating LR sequence, and end RLL sequence); and (ii) GIN 30 (SEQ ID No. 18), which is a peptide constructed from a region of apolipoprotein J, which has been reported to consist of an amphipathic alpha helix (Bailey et al., Biochemistry 2001; 40:11828-40), i.e. human apolipoprotein $J_{331-349}$ having amino acid sequence LQVAERLTRKYNELLKSYQ.

As shown in FIG. 4 of the Example, none of the peptides GIN 17, GIN 27, GIN 28 and GIN 30 showed any antiviral activity. However, to the inventor's surprise, he found that only the tandem repeat peptide modified from ApoB in accordance with the first aspect of the invention, i.e. GIN16, had any appreciable antiviral effect against herpes simplex virus type HSV1. This data was particularly surprising because blockage of LDL receptors would not be expected to inhibit HSV1 infection, as this virus is not considered to use LDL receptors to enter and thereby infect cells.

Therefore, following this surprising discovery of the antiviral properties of GIN 16, the inventor produced and investigated the antiviral activity of a number of derivatives or modifications of GIN 16. He was surprised to find that several of these also possessed antiviral properties, whereas some did not. Surprisingly, peptides according to the first aspect of the invention, i.e. peptides comprising a tandem repeat region derived from an HSPG receptor binding region of apolipoprotein B, exhibited antiviral properties.

There is further evidence to suggest that, surprisingly, simple usage of tandem repeats of any HSPG binding regions from any apolipoproteins do not necessarily result in a peptide, which exhibits antiviral activity. For example:—

1. GIN 14 is a tandem repeat derived from the second HSPG receptor binding region of apoe (SEQ ID No.19), but has no antiviral activity; and
2. Azuma et al. discussed supra, discloses anti-bacterial activity for $apoE_{133-162}$, also describes how peptides from a range of heparin-binding regions (including apoB, VEGF, PACAP and Vn) did not have antibacterial activity. Thus, the broader antimicrobial properties ascribed to certain peptides derived from heparin binding regions by Azuma, does not apply to most examples of peptides derived from such regions.

In conclusion, unexpectedly, tandem repeat peptides in accordance with the first aspect of the invention (i.e. those which are derived from an HSPG receptor binding region of apolipoprotein B) have antiviral activity.

While the inventor does not wish to be bound by any hypothesis, he has realised that one possible mode of interaction between HSV1 virus and the apolipoprotein apoB is due to the fact that both of these use cellular heparan sulphate proteoglycan (HSPG) molecules as their initial site of binding to cells, before subsequent attachment to secondary receptors. Hence, the inventor has suggested that competition between HSV1 virus and apoB, which contains lipoproteins, could occur at these HSPG sites, and that this may affect viral entry. The inventor suggests that this antiviral activity of GIN 16 may be due to either blockage of HSPG sites on cell surfaces, since some viruses use these as initial attachment sites (whereas only a limited number have been reported to use LDL receptors). Accordingly, the inventor suggested that this is one possible reason why peptides derived from an HSPG receptor binding region of apolipoprotein B in accordance with the first aspect of the present invention, exhibit anti-viral activity.

Hence, it is preferred that the peptide according to the first aspect of the invention comprises a tandem repeat of $apoB_{3359-3367}$ of SEQ ID No.2, or a truncation thereof.

By the expression "a tandem repeat of $apoB_{3359-3367}$ of SEQ ID No.2", we mean the peptide substantially comprises an amino acid sequence: RLTRKRGLKRLTRKRGLK, i.e. an 18-mer (SEQ ID No.2). Hence, the tandem repeat of $apoB_{3359-3367}$ of SEQ ID No.2 preferably, comprises a repeat of the amino acid sequence: RLTRKRGLK, i.e. a 9-mer (SEQ ID No.1). For the sake of clarity, the tandem repeat of $apoB_{3359-3367}$ of SEQ ID No.2 (18-mer) is a dimer repeat (2×) of the amino acid sequence RLTRKRGLK of SEQ ID No.1 (9-mer).

By "a truncation of SEQ ID No.2" we mean that the tandem repeat (e.g. the 18 mer of SEQ ID No. 2) is reduced in size by removal of amino acids. The reduction of amino acids may be by removal of residues from the C or N terminal of the peptide or may be by deletion of one or more amino acids from within the core of the peptide (i.e. amino acids 2-17 of SEQ ID No. 2).

Table 1 below illustrates the amino acid sequence of $apoB_{3359-3367}$ (i.e the 9-mer of SEQ ID No.1), aligned with corresponding amino acids of other preferred peptides according to the first aspect of the invention (see the Examples). It will be appreciated that this 9-mer is repeated in peptides according to the present invention.

TABLE 1

Analysis of effective peptide sequences exhibiting antiviral properties

| 1 | 2 | 3 | 4 | 5 | 6 | 7 | 8 | 9 | | |
|---|---|---|---|---|---|---|---|---|---|---|
| **R** | **L** | **T** | **R** | **K** | **R** | **G** | **L** | **K** | apoB 3359-3367 | SEQ ID No. 1 |
| L | R | **T** | **R** | **K** | **R** | **G** | R | **K** | GIN 16 | Residues 1 to 9 of SEQ ID No. 48 |
| W | R | W | **R** | **K** | **R** | W | R | **K** | GIN 33 | Residues 1 to 9 of SEQ ID No. 7 |
| | R | **T** | **R** | **K** | **R** | **G** | R | **K** | GIN 35 | Residues 1 to 8 of SEQ ID No. 3 |
| | R | **T** | **R** | **K** | **R** | **G** | R | R | GIN 36 | Residues 1 to 8 of SEQ ID No. 4 |
| L | R | K | **R** | **K** | **R** | L | | | GIN 37 | Residues 1 to 7 of SEQ ID No. 5 |
| L | R | K | **R** | **K** | **R** | L | R | **K** | GIN 38 | Residues 1 to 9 of SEQ ID No. 6 |
| L | R | K | L | R | K | R | **L** | L | GIN 1p | SEQ ID No. 24 |

Indicates residue is the same as that in apoB 3359-3367

In the light of this alignment data the inventor realised that there was a recurring amino acid motif in active peptides derived from SEQ ID No. 2. This motif corresponds to a tripeptide: Arginine-Lysine-Arginine (RKR), which is found at amino acids 4, 5, 6 and 13, 14, 15 of SEQ ID. No 2. It is therefore preferred that peptides according to the present invention comprise two RKR motifs.

Preferably, the peptide according to the first aspect comprises a tandem repeat of $apoB_{3359-3367}$ of SEQ ID No.2 or a truncation thereof, characterised in that at least one amino acid residue, other than the RKR motifs, has been replaced by a Glycine (G), Threonine (T), Histidine (H), Tryptophan (W), Arginine (R) or Leucine (L) residue or derivatives thereof.

Suitably, one or more, more suitably, two or more, and even more suitably, three or more amino acid residues may be replaced by a Glycine (G), Threonine (T), Histidine (H), Tryptophan (W), Arginine (R) or Leucine (L) residue or derivative thereof. Preferably, four or more, more preferably, five or more, and even more preferably, six or more amino acid residues may be replaced by these amino acids or derivative thereof. Preferably, the replaced or substituted residue is the first, second, third, seventh, eighth, ninth, tenth, eleventh, twelfth, sixteenth, seventeenth or eighteenth residue of SEQ ID No. 2.

The polypeptide according to the invention may comprise 18 amino acids (or derivatives thereof) and thereby correspond to the full length of SEQ ID No. 2 with or without the substitutions discussed above. However, the inventors have surprisingly found that truncated peptides based on SEQ ID No.2 also have efficacy as antiviral agents. Accordingly, preferred peptides or derivatives thereof may have less than 18 amino acids. For instance, some peptides according to the first aspect of the invention may be 17, 16, 15, 14, 13, 12, 11, 10 or less amino acids in length. Deletions are preferably made at positions 1, 2, 8, 9, 10, 11, 17 and/or 18 of SEQ ID No. 2.

The polypeptide according to the first aspect may preferably have formula I:

{abcRKRxyz}+{a'b'c'RKRx'y'z'} wherein a & a'=is independently selected from a positively charged residue, which may be selected from either Arginine (R) or Lysine (K) or Histidine (H); Leucine (L); Tryptophan (W); or is deleted;

b & b'=is independently selected from Leucine (L); Arginine (R); Lysine (K); or is deleted;

c & c'=is independently selected from Threonine (T); Tryptophan (W); or a positively charged residue, which may be selected from Arginine (R) or Lysine (K) or Histidine (H);

x & x'=is independently selected from Glycine (G); Tryptophan (W); Leucine (L); or a positively charged residue, which may be selected from Arginine (R) or Lysine (K) or Histidine (H);

y & y'=is independently selected from Leucine (L); a positively charged residue, which may be selected from Arginine (R) or Lysine (K) or Histidine (H); or is deleted;

z & z'=is independently selected from a positively charged residue, which may be selected from Arginine (R) or Lysine (K) or Histidine (H); or Leucine; or is deleted.

The polypeptide according to the first aspect may preferably have formula II:

{abcRKRxyz}+{abcRKRxyz} wherein a=is independently selected from a positively charged residue, which may be selected from either Arginine (R) or Lysine (K) or Histidine (H); Leucine (L); Tryptophan (W); or is deleted;

b=is independently selected from Leucine (L); Arginine (R); Lysine (K); or is deleted;

c=is independently selected from Threonine (T); Tryptophan (W); or a positively charged residue, which may be selected from Arginine (R) or Lysine (K) or Histidine (H);

x=is independently selected from Glycine (G); Tryptophan (W); Leucine (L); or a positively charged residue, which may be selected from Arginine (R) or Lysine (K) or Histidine (H);

y=is independently selected from Leucine (L); a positively charged residue, which may be selected from Arginine (R) or Lysine (K) or Histidine (H); or is deleted;

z=is independently selected from a positively charged residue, which may be selected from Arginine (R) or Lysine (K) or Histidine (H); or Leucine (L); or is deleted.

The polypeptide according to the first aspect may preferably have formula III:

{abcRKRxyz}+{abcRKRxyz} wherein a=is independently selected from Tryptophan (W); Arginine (R); Leucine (L); or is deleted;

b=is independently selected from Leucine (L); Arginine (R) or Lysine (K); or is deleted;

c=is independently selected from Tryptophan (W); Threonine (T); Lysine (K);

x=is independently selected from Tryptophan (W); Glycine (G); Leucine (L); Arginine (R);

y=is independently selected from Leucine (L); a positively charged residue, which may be selected from Arginine (R) or Lysine (K) or Histidine (H); or is truncated here;

z=is independently selected from a positively charged residue, which may be selected from Arginine (R) or Lysine (K) or Histidine (H); or Leucine (L); or is truncated here.

The inventor has also appreciated that peptides may be employed according to the invention that comprise more than just a tandem dimer repeat of $apoB_{3359-3367}$ of SEQ ID No.2, or a truncation thereof. For example, peptides comprising a trimer, or tetramer, or even greater number of repeats of SEQ ID No.1 may be employed as useful antiviral agents.

Accordingly, it is preferred that the polypeptide may preferably have formula IV:

$$\{abcRKRxyz\}^n$$

wherein a, b, c, x, y, and z are as defined above with reference to formula I, II or III, and wherein n is equal to 2, 3, 4 or 5, or more.

Other preferred peptides may comprise repeats of the 18 mer peptide (or truncation thereof) defined by formula I (e.g. repeats of a heterodimer of the 9 mers comprising the peptide of formula I).

Preferred peptides according to the first aspect of the invention comprise the amino acid sequence:

- (a) LRTRKRGRKLRTRKRGRK (SEQ ID No.48). This peptide is designated GIN 16 when referred to herein;
- (b) RTRKRGRKRTRKRGRK (SEQ ID No.3). This peptide is designated GIN 35 when referred to herein;
- (c) RTRKRGRRTRKRGR (SEQ ID No.4). This peptide is designated GIN 36 when referred to herein;
- (d) LRKRKRLLRKRKRL (SEQ ID No.5). This peptide is designated GIN 37 when referred to herein; and
- (e) LRKRKRLRKLRKRKRLRK (SEQ ID No.6). This peptide is designated GIN 38 when referred to herein;
- (f) WRWRKRWRKWRWRKRWRK (SEQ ID No.7). This peptide is designated GIN 33 when referred to herein.
- (g) RRWRKRWRKWRWRKRWRK (SEQ ID No.34). This peptide is designated MU 28 when referred to herein.
- (h) KRWRKRWRKWRWRKRWRK (SEQ ID No.35). This peptide is designated MU 29 when referred to herein.
- (i) LRWRKRWRKWRWRKRWRK (SEQ ID No.36). This peptide is designated MU 30 when referred to herein.
- (j) HRWRKRWRKWRWRKRWRK (SEQ ID No.37). This peptide is designated MU 31 when referred to herein.
- (k) RWRKRWRKWRWRKRWRK (SEQ ID No.38). This peptide is designated MU 32 when referred to herein. (I) RRWRKRWRKRRWRKRWRK (SEQ ID No.39). This peptide is designated MU 33 when referred to herein.
- (m)KRWRKRWRKKRWRKRWRK (SEQ ID No.40). This peptide is designated MU 34 when referred to herein.
- (n) LRWRKRWRKLRWRKRWRK (SEQ ID No.41). This peptide is designated MU 35 when referred to herein.
- (o) HRWRKRWRKHRWRKRWRK (SEQ ID No.42). This peptide is designated MU 36 when referred to herein.
- (p) RWRKRWRKRWRKRWRK (SEQ ID No.43). This peptide is designated MU 37 when referred to herein.
- (q) RWRKRGRKRWRKRGRK (SEQ ID No.44). This peptide is designated MU 69 when referred to herein.
- (r) RTRKRWRKRTRKRGRK (SEQ ID No.45). This peptide is designated MU 70 when referred to herein.
- (s) RWRKRWRKRWRKRWRK (SEQ ID No.46). This peptide is designated MU 71 when referred to herein.
- (t) RWRKRWRWRKRWRWRKRW (SEQ ID No.47). This peptide is designated MU 84 when referred to herein.

According to a second aspect of the present invention, there is provided a polypeptide, derivative or analogue thereof according to the first aspect of the invention, for use as a medicament.

According to a third aspect of the invention, there is provided use of a polypeptide, derivative or analogue thereof according to the first aspect of the invention, for the manufacture of a medicament for treating a viral infection.

It will be appreciated that the therapeutic effects of polypeptides, derivatives or analogues according to the invention may be mediated "indirectly" by agents that increase the activity of such polypeptides, derivatives or analogues. The present invention provides the first medical use of such agents.

Thus, according to a fourth aspect of the invention, there is provided an agent capable of increasing the biological activity of a polypeptide, derivative or analogue according to the first aspect of the invention for use as a medicament.

Agents capable of increasing the biological activity of polypeptides, derivatives or analogues according to the invention may achieve their effect by a number of means. For instance, such agents may increase the expression of such polypeptides, derivatives or analogues. Alternatively (or in addition), such agents may increase the half-life of polypeptides, derivatives or analogues according to the invention in a biological system, for example, by decreasing turnover of the polypeptides, derivatives or analogues.

Due to their increased biological activity, polypeptides, derivatives or analogues according to the invention are of utility as antiviral agents.

Polypeptides, derivatives or analogues according to the invention may be used in the treatment of a number of viral infections. The virus may be any virus, and particularly an enveloped virus. Preferred viruses are poxviruses, iridoviruses, togaviruses, or toroviruses. A more preferred virus is a filovirus, arenavirus, bunyavirus, or a rhabdovirus. An even more preferred virus is a paramyxovirus or an orthomyxovirus. It is envisaged that the virus may preferably include a hepadnavirus, coronavirus, flavivirus, or a retrovirus. Preferably, the virus includes a herpesvirus or a lentivirus. In preferred embodiments, the virus may be Human Immunodeficiency Virus (HIV), Human herpes simplex virus type 2 (HSV2), or Human herpes simplex virus type 1 (HSV1).

Polypeptides, derivatives or analogues according to the invention may be used to treat viral infections as a monotherapy or in combination with other compounds or treatments used in antiviral therapy (e.g. acyclovir, gangcylovir, ribavirin, interferon, anti-HIV medicaments including nucleoside, nucleotide or non-nucleoside inhibitors of reverse transcriptase, protease inhibitors and fusion inhibitors.)

Peptides, and derivatives thereof, according to the present invention preferably have an efficacy for inhibiting viral growth such that their $IC_{50}$ value is 30 μM or less. It is preferred that the $IC_{50}$ value is 20 μM or less and more preferred that the $IC_{50}$ value is 10 μM or less.

Preferred peptides have similar $IC_{50}$ values between viral species. For instance preferred peptides have similar $IC_{50}$ values for inhibiting HSV1, HSV2 and HIV growth.

It will be appreciated that modified amino acids may be substituted, into the tandem repeat of apoB according to the invention, with a number of amino acid variants that may be known to those skilled in the art. Such peptides will still have antiviral activity provided that the modification does not significantly alter its chemical characteristics. For instance, hydrogens on the side chain amines of R or K may be replaced with methylene groups ($—NH_2 \rightarrow —NH(Me)$ or $—N(Me)_2$). Furthermore, the N-terminal amino group of the peptides may be protected by reacting with a carboxylic acid and the C-terminal carboxyl group of the peptide may be protected by reacting with an amine.

Derivatives of polypeptides according to the invention may also include derivatives that increase or decrease the polypeptide's half-life in vivo. Examples of derivatives capable of increasing the half-life of polypeptides according to the invention include peptoid derivatives of the polypeptides, D-amino acid derivatives of the polypeptides, and peptide-peptoid hybrids.

Polypeptides according to the invention may be subject to degradation by a number of means (such as protease activity in biological systems). Such degradation may limit the bioavailability of the polypeptides and hence the ability of the polypeptides to achieve their biological function. There are wide ranges of well-established techniques by which peptide derivatives that have enhanced stability in biological contexts can be designed and produced. Such peptide derivatives may have improved bioavailability as a result of increased resistance to protease-mediated degradation. Preferably, a peptide derivative or analogue suitable for use according to the invention is more protease-resistant than the peptide from which it is derived. Protease-resistance of a peptide derivative and the peptide from which it is derived may be evaluated by means of well-known protein degradation assays. The relative values of protease resistance for the peptide derivative and peptide may then be compared.

Peptoid derivatives of the peptides of the invention may be readily designed from knowledge of the structure of the peptide according to the first or second aspect of the invention. Commercially available software may be used to develop peptoid derivatives according to well-established protocols.

Retropeptoids, (in which all amino acids are replaced by peptoid residues in reversed order) are also able to mimic antiviral peptides derived from apolipoproteins. A retropeptoid is expected to bind in the opposite direction in the ligand-binding groove, as compared to a peptide or peptoid-peptide hybrid containing one peptoid residue. As a result, the side chains of the peptoid residues are able point in the same direction as the side chains in the original peptide.

A further embodiment of a modified form of polypeptide according to the invention comprises D-amino acid forms of the polypeptide. The preparation of peptides using D-amino acids rather than L-amino acids greatly decreases any unwanted breakdown of such an agent by normal metabolic processes, decreasing the amounts of agent which needs to be administered, along with the frequency of its administration.

The polypeptides, analogues, or derivatives of the invention represent products that may advantageously be expressed by biological cells.

Thus, the present invention also provides, in a fifth aspect, a nucleic acid sequence encoding a polypeptide, derivative or analogue according to the first aspect of the invention.

Preferred nucleic acids according to the fifth aspect of the invention encode $apoB_{3359-3367}$, GIN 16, GIN 35, GIN 36, GIN 37, GIN 38 and GIN 33 with the respective nucleic acid sequences:

```
                                        (SEQ ID No. 8)
cgtcttactc gtaaacgtgg tcttaaacgt cttactcgta
aacgtggtct taaa;

                                        (SEQ ID No. 9)
cttcgtactc gtaaacgtgg tcgtaaactt cgtactcgta
aacgtggtcg taaa;

                                       (SEQ ID No. 10)
cgtactcgta aacgtggtcg taaacgtact cgtaaacgtg
gtcgtaaa;
```

-continued

```
                                       (SEQ ID No. 11)
cgtactcgta aacgtggtcg tcgtactcgt aaacgtggtc gt;

                                       (SEQ ID No. 12)
cttcgtaaac gtaaacgtct tcttcgtaaa cgtaaacgtc tt;

                                       (SEQ ID No. 13)
cttcgtaaac gtaaacgtct tcgtaaactt cgtaaacgta
aacgtcttcg taaa;
and

                                       (SEQ ID No. 14)
tggcgttggc gtaaacgttg gcgtaaatgg cgttggcgta
aacgttggcg taaa.
```

A skilled person will appreciate that the nucleic acid sequences of other preferred peptides according to the present invention may be readily generated.

Due to the degeneracy of the genetic code, it is clear that any nucleic acid sequence could be varied or changed without substantially affecting the sequence of the peptide encoded thereby, to provide a functional variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of, sequence which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid.

It will be appreciated that polypeptides, derivatives and analogues according to the invention represent favourable agents to be administered by techniques involving cellular expression of nucleic acid sequences encoding such molecules. Such methods of cellular expression are particularly suitable for medical use in which the therapeutic effects of the polypeptides, derivatives and analogues are required over a prolonged period.

Thus according to a sixth aspect of the present invention there is provided a nucleic acid sequence according to the fifth aspect of the invention for use as a medicament.

The nucleic acid may preferably be an isolated or purified nucleic acid sequence. The nucleic acid sequence may preferably be a DNA sequence.

The nucleic acid sequence may further comprise elements capable of controlling and/or enhancing its expression. The nucleic acid molecule may be contained within a suitable vector to form a recombinant vector. The vector may for example be a plasmid, cosmid or phage. Such recombinant vectors are highly useful in the delivery systems of the invention for transforming cells with the nucleic acid molecule.

Recombinant vectors may also include other functional elements. For instance, recombinant vectors can be designed such that the vector will autonomously replicate in the cell. In this case elements that induce nucleic acid replication may be required in the recombinant vector. Alternatively, the recombinant vector may be designed such that the vector and recombinant nucleic acid molecule integrates into the genome of a cell. In this case nucleic acid sequences, which favour targeted integration (e.g. by homologous recombination) are desirable. Recombinant vectors may also comprise DNA coding for genes that may be used as selectable markers in the cloning process.

The recombinant vector may also further comprise a promoter or regulator to control expression of the gene as required.

The nucleic acid molecule may (but not necessarily) be one, which becomes incorporated in the DNA of cells of the subject being treated. Undifferentiated cells may be stably transformed leading to the production of genetically modified daughter cells (in which case regulation of expression in the subject may be required e.g. with specific transcription factors or gene activators). Alternatively, the delivery system may be designed to favour unstable or transient transformation of differentiated cells in the subject being treated. When this is the case, regulation of expression may be less important because expression of the DNA molecule will stop when the transformed cells die or stop expressing the protein (ideally when the required therapeutic effect has been achieved).

The delivery system may provide the nucleic acid molecule to the subject without it being incorporated in a vector. For instance, the nucleic acid molecule may be incorporated within a liposome or virus particle. Alternatively a "naked" nucleic acid molecule may be inserted into a subject's cells by a suitable means, e.g. direct endocytotic uptake.

The nucleic acid molecule may be transferred to the cells of a subject to be treated by transfection, infection, microinjection, cell fusion, protoplast fusion or ballistic bombardment. For example, transfer may be by ballistic transfection with coated gold particles, liposomes containing the nucleic acid molecule, viral vectors (e.g. adenovirus) and means of providing direct nucleic acid uptake (e.g. endocytosis) by application of the nucleic acid molecule directly.

It will be appreciated that the polypeptides, agents, nucleic acids or derivatives according to the present invention may be used in a monotherapy (i.e. use of polypeptides, agents, nucleic acids or derivatives according to the invention alone to prevent and/or treat a viral infection). Alternatively, polypeptides, agents, nucleic acids or derivatives according to the invention may be used as an adjunct, or in combination with known therapies.

Polypeptides, agents, nucleic acids or derivatives according to the invention may be combined in compositions having a number of different forms depending, in particular, on the manner in which the composition is to be used. Thus, for example, the composition may be in the form of a powder, tablet, capsule, liquid, ointment, cream, gel, hydrogel, aerosol, spray, micelle, transdermal patch, liposome or any other suitable form that may be administered to a person or animal. It will be appreciated that the vehicle of the composition of the invention should be one which is well tolerated by the subject to whom it is given, and preferably enables delivery of the polypeptides, agents, nucleic acids or derivatives to the brain. It is preferred that the polypeptides, agents, nucleic acids or derivatives according to the invention be formulated in a manner that permits their passage across the blood brain barrier.

Compositions comprising polypeptides, agents, nucleic acids or derivatives according to the invention may be used in a number of ways. For instance, oral administration may be required in which case the compound may be contained within a composition that may, for example, be ingested orally in the form of a tablet, capsule or liquid. Alternatively the composition may be administered by injection into the blood stream. Injections may be intravenous (bolus or infusion) or subcutaneous (bolus or infusion). The compounds may be administered by inhalation (e.g. intranasally).

Compositions may be formulated for topical use. For instance, ointments may be applied to the skin, areas in and around the mouth or genitals to treat specific viral infections. Topical application to the skin is particularly useful for treating viral infections of the skin or as a means of transdermal delivery to other tissues. Intravaginal administration is effective for treating sexually transmitted diseases (including AIDS).

Polypeptides, agents, nucleic acids or derivatives may also be incorporated within a slow or delayed release device. Such devices may, for example, be inserted on or under the skin, and the compound may be released over weeks or even months. Such devices may be particularly advantageous when long term treatment with a polypeptide, agent, nucleic acid or derivative according to the invention is required and which would normally require frequent administration (e.g. at least daily injection).

It will be appreciated that the amount of a polypeptide, agent, nucleic acid or derivative that is required is determined by its biological activity and bioavailability which in turn depends on the mode of administration, the physicochemical properties of the polypeptide, agent, nucleic acid or derivative employed and whether the polypeptide, agent, nucleic acid or derivative is being used as a monotherapy or in a combined therapy. The frequency of administration will also be influenced by the above-mentioned factors and particularly the half-life of the polypeptide, agent, nucleic acid or derivative within the subject being treated.

Optimal dosages to be administered may be determined by those skilled in the art, and will vary with the particular polypeptide, agent, nucleic acid or derivative in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of polypeptides, agents, nucleic acids or derivatives according to the invention and precise therapeutic regimes (such as daily doses of the polypeptides, agents, nucleic acids or derivatives and the frequency of administration).

Generally, a daily dose of between 0.01 μg/kg of body weight and 0.5 g/kg of body weight of polypeptides, agents, nucleic acids or derivatives according to the invention may be used for the prevention and/or treatment of a viral infection, depending upon which specific polypeptide, agent, nucleic acid or derivative is used. More preferably, the daily dose is between 0.01 mg/kg of body weight and 200 mg/kg of body weight, and most preferably, between approximately 1 mg/kg and 100 mg/kg.

Daily doses may be given as a single administration (e.g. a single daily injection). Alternatively, the polypeptide, agent, nucleic acid or derivative used may require administration twice or more times during a day. As an example, polypeptides, agents, nucleic acids or derivatives according to the invention may be administered as two (or more depending upon the severity of the condition) daily doses of between 25 mg and 7000 mg (i.e. assuming a body weight of 70 kg). A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention provides a pharmaceutical composition comprising a therapeutically effective amount of a polypeptide, agent, nucleic acid or derivative according to the invention and optionally a pharmaceutically acceptable vehicle. In one embodiment, the amount of the polypeptide, agent, nucleic acid or derivative is an amount from about 0.01 mg to about 800 mg. In another embodiment, the amount of the polypeptide, agent, nucleic acid or derivative is an amount from about 0.01 mg to about 500 mg. In another embodiment, the amount of the polypeptide, agent, nucleic acid or derivative is an amount from about 0.01 mg to about 250 mg. In another embodiment, the amount of the polypeptide, agent, nucleic acid or derivative is an amount from about 0.1 mg to about 60 mg. In another embodiment, the amount of the polypeptide, agent, nucleic acid or derivative is an amount from about 0.1 mg to about 20 mg.

This invention provides a process for making a pharmaceutical composition comprising combining a therapeutically effective amount of a polypeptide, agent, nucleic acid or derivative according to the invention and a pharmaceutically acceptable vehicle. A "therapeutically effective amount" is any amount of a polypeptide, agent, nucleic acid or derivative according to the invention which, when administered to a subject provides prevention and/or treatment of a viral infection. A "subject" is a vertebrate, mammal, domestic animal or human being.

A "pharmaceutically acceptable vehicle" as referred to herein is any physiological vehicle known to those of ordinary skill in the art useful in formulating pharmaceutical compositions.

In a preferred embodiment, the pharmaceutical vehicle is a liquid and the pharmaceutical composition is in the form of a solution. In another embodiment, the pharmaceutically acceptable vehicle is a solid and the composition is in the form of a powder or tablet. In a further embodiment, the pharmaceutical vehicle is a gel and the composition is in the form of a cream or the like.

A solid vehicle can include one or more substances which may also act as flavouring agents, lubricants, solubilisers, suspending agents, fillers, glidants, compression aids, binders or tablet-disintegrating agents; it can also be an encapsulating material. In powders, the vehicle is a finely divided solid that is in admixture with the finely divided active polypeptide, agent, nucleic acid or derivative. In tablets, the active polypeptide, agent, nucleic acid or derivative is mixed with a vehicle having the necessary compression properties in suitable proportions and compacted in the shape and size desired. The powders and tablets preferably contain up to 99% of the active polypeptide, agent, nucleic acid or derivative. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions, syrups, elixirs and pressurized compositions. The active polypeptide, agent, nucleic acid or derivative can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The polypeptide, agent, nucleic acid or derivative may be prepared as a sterile solid composition that may be dissolved or suspended at the time of administration using sterile water, saline, or other appropriate sterile injectable medium. Vehicles are intended to include necessary and inert binders, suspending agents, lubricants, flavourants, sweeteners, preservatives, dyes, and coatings.

Polypeptides, agents, nucleic acids or derivatives according to the invention can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like.

Polypeptides, agents, nucleic acids or derivatives according to the invention can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

All of the features described herein (including any accompanying claims, abstract and drawings), and/or all of the steps of any method or process so disclosed, may be combined with any of the above aspects in any combination, except combinations where at least some of such features and/or steps are mutually exclusive.

Embodiments of the invention will now be further described, by way of example only, with reference to the following Examples and figures in which:—

EXAMPLE 1

Experiments were initially conducted with: (i) a tandem repeat of Apo$E_{141-149}$ (Apo$E_{141-149dp}$) from a HSPG receptor binding region of apolipoprotein E; and (ii) Apo$E_{263-286}$ from a region of apolipoprotein E that is not involved in HSPG receptor binding. These experiments were conducted to establish whether or not peptide (i) had any efficacy as an antiviral agent. The results from this body of work motivated the inventor to investigate the efficacy of other peptides—including peptides according to the present invention (see later Examples).

1.1 HSV1

Figure 1:
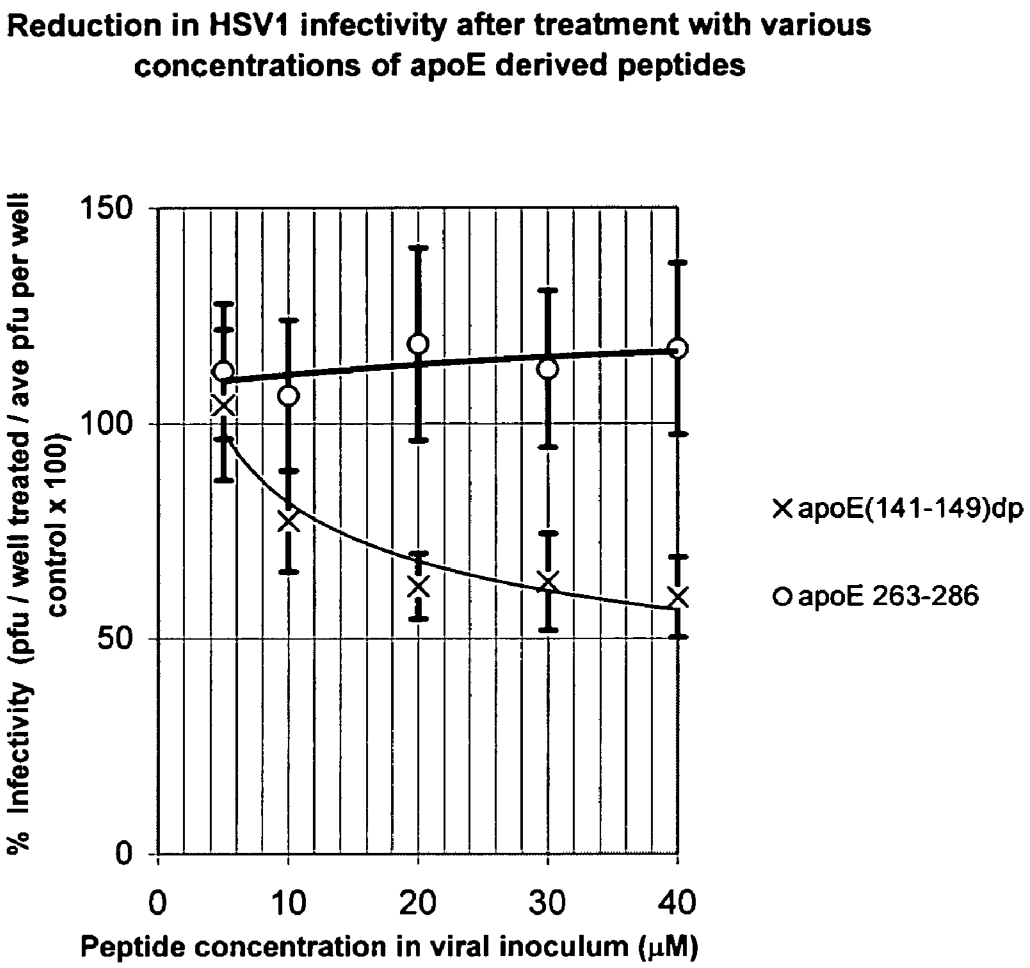
FIG. 1 shows the effect of apo$E_{141-149dp}$ and apo$E_{263-286}$ on HSV1 infectivity. (points are derived from the average of up to four values) as described in Example 1.

FIG. 1 and table 1 show typical results for the test for anti-HSV1 activity. The assay involved treating confluent Vero cells in 24-well plates with medium containing virus and varying amounts of peptide for one hour, followed by removal of this inoculum, and addition of viscous 'overlay' medium, containing 0.2% high viscosity carboxymethylcellulose. The overlay medium only allows infection of those cells immediately adjacent to an infected cell. After 2 days incubation and then fixation and staining, small patches of infected cells (or 'plaques') are visible, which are counted. Each of these corresponds to the infection of a single cell during the one hour inoculation. $ApoE_{141-149dp}$ produced a 40% reduction in plaque number at a concentration of around 20 μM. Note the peptide was only present in the experimental system for 1 hour.

TABLE 1

HSV1 plaque formation in Vero cells after inoculation with virus containing either $apoE_{141-149\ dp}$ or $apoE_{263-286}$.
Plaque number

| | $ApoE_{141-149\ dp}$ | | | | | $ApoE_{263-286}$ | | | | |
|---|---|---|---|---|---|---|---|---|---|---|
| [μM] | 1 | 2 | 3 | 4 | Mean ± sd | 1 | 2 | 3 | 4 | Mean ± sd |
| 0 | 96 | 102 | 123 | | 107 ± 14.2 | | | | | |
| 5 | 129 | 106 | 103 | 100 | 110 ± 13.2 | 113 | 119 | 122 | 126 | 120 ± 5.5 |
| 10 | 73 | 87 | 76 | 89 | 81 ± 7.9 | 116 | 124 | 102 | | 114 ± 11.1 |
| 20 | 68 | 67 | 63 | 63 | 65 ± 2.6 | 148 | 112 | 133 | 114 | 127 ± 17.0 |
| 30 | 72 | 71 | 56 | | 66 ± 9.0 | 134 | 109 | 114 | 125 | 121 ± 11.2 |
| 40 | 64 | 65 | 53 | 68 | 63 ± 6.6 | 120 | 113 | 125 | 144 | 126 ± 11.2 |

Values for untreated wells are underlined.

1.2 HSV2

Figure 2:
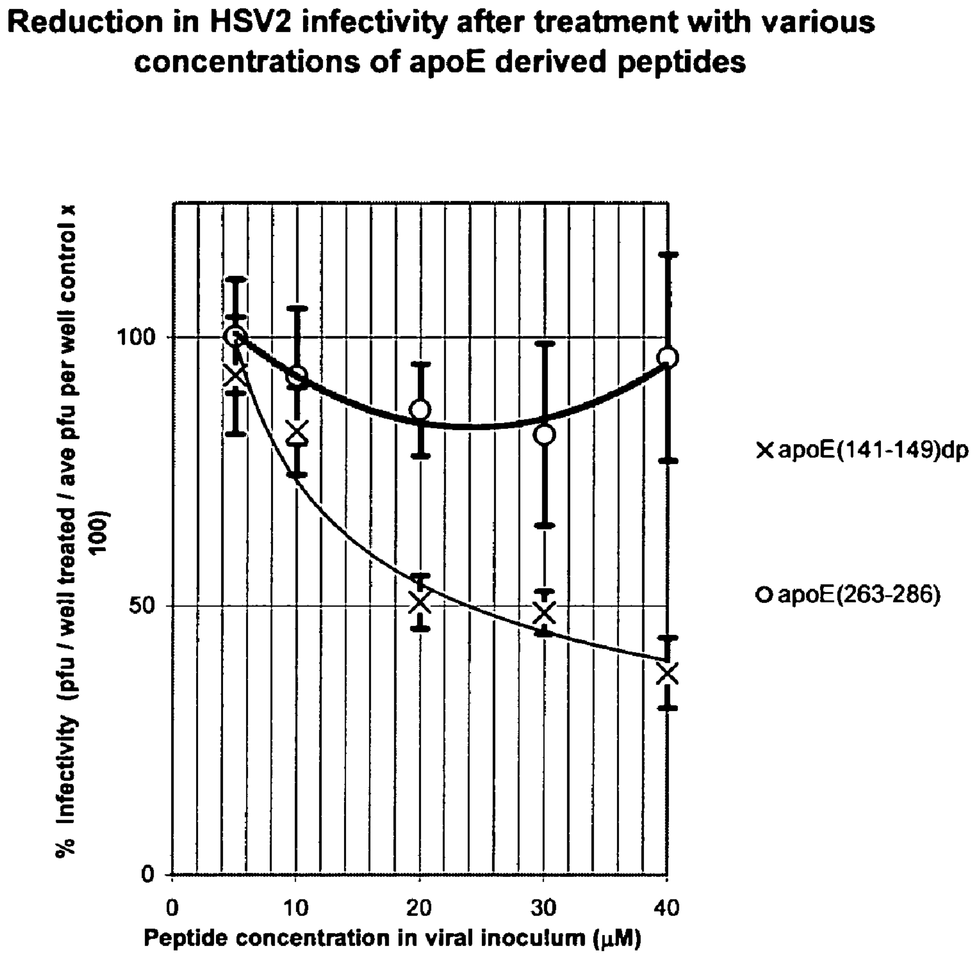
FIG. 2 shows the effect of apo$E_{141-149dp}$ or apo$E_{263-286}$ on HSV2 infectivity (points are derived from the average of up to four values) as described in Example 1.

FIG. 2 and table 2 show typical results for the test for anti-HSV2 activity. The assay was carried out as for the anti-HSV1 assay, except Hep-2 cells were used rather than Vero cells. $ApoE_{141-149dp}$ produced a 50% reduction in plaque number at a concentration of around 20 μM. Again note that the peptide was only present in the experimental system for 1 hour.

TABLE 2

HSV2 plaque formation in HEp-2 cells after inoculation with virus containing either $apoE_{141-149\ dp}$ or $apoE_{263-286}$.
Plaque number

| | $ApoE_{141-149\ dp}$ | | | | | $ApoE_{263-286}$ | | | | |
|---|---|---|---|---|---|---|---|---|---|---|
| [μM] | 1 | 2 | 3 | 4 | Mean ± sd | 1 | 2 | 3 | 4 | Mean ± sd |
| 0 | 156 | 137 | 162 | 152 | 152 ± 10.7 | | | | | |
| 5 | 160 | 134 | 140 | 130 | 141 ± 13.3 | 135 | 160 | 161 | 152 | 152 ± 12.0 |
| 10 | 125 | 113 | 131 | 132 | 125 ± 8.7 | 157 | 121 | 151 | 134 | 141 ± 16.1 |
| 20 | 82 | 72 | 73 | 81 | 77 ± 5.2 | 118 | 150 | 182 | 134 | 146 ± 27.3 |
| 30 | 76 | 77 | 71 | 72 | 74 ± 2.9 | 118 | 117 | 103 | 159 | 124 ± 24.2 |
| 40 | 51 | 59 | 69 | 49 | 57 ± 9.1 | 132 | 144 | 125 | 124 | 131 ± 24.2 |

Values for untreated wells are underlined.

1.3. HIV

Figure 3:
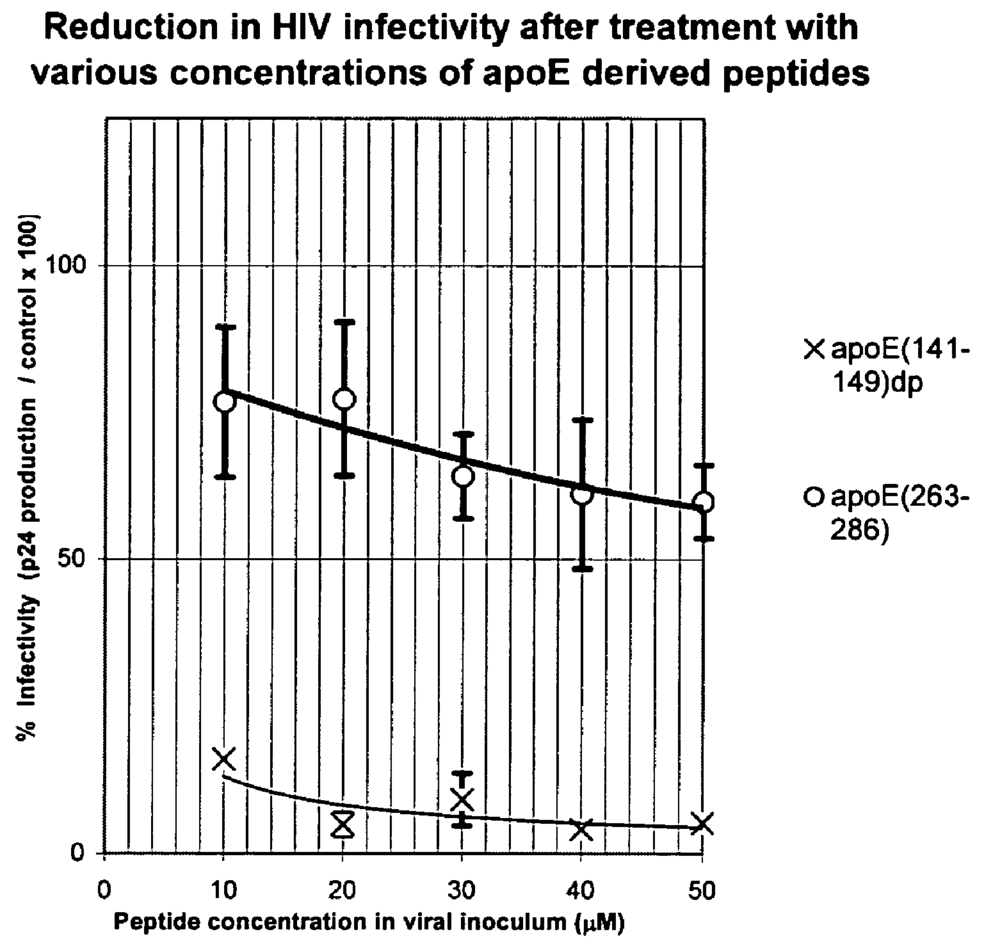
FIG. 3 illustrates inhibition of HIV-1 p24 production, as measured by ELISA, by apo$E_{141-149dp}$, and apo$E_{263-286}$ in acutely infected U937 cells (values are the average of three experiments) as described in Example 1.

FIG. 3 and table 3 show typical results for the test for anti-HIV activity. The assay was carried out by incubating HIV infected U937 cells in the presence of various levels of peptide for 7 days, followed by assay for levels of the HIV protein p24 in the cells using an Enzyme Linked Immunoabsorbant Assay (ELISA) technique. $ApoE_{141-149dp}$ produced a 95% reduction in infectivity at 20 μM. $ApoE_{263-286}$ produced a 20% reduction in infectivity at 20 μM.

The effect on HIV appears at lower peptide concentrations, though this may be due to peptide being in contact with cells for 7 days, as opposed to just 1 hour in plaque reduction assays with herpes viruses. Alternatively the different activities may be due to differences between assay systems.

TABLE 3

Inhibition of HIV-1 p24 production, as measured by ELISA, by $apoE_{141\text{-}149\,dp}$, and $apoE_{263\text{-}286}$ in acutely infected U937 cells.
% Decrease in HIV p24 Production

| | $ApoE_{141\text{-}149\,dp}$ | | | | $ApoE_{263\text{-}286}$ | | | |
|---|---|---|---|---|---|---|---|---|
| [μM] | Exp. 1 | Exp. 2 | Exp. 3 | Mean ± sd | Exp. 1 | Exp. 2 | Exp. 3 | Mean ± sd |
| 0 | 0 | 0 | 0 | 0 | 0 | 0 | 0 | 0 |
| 10 | 91.66 | 70.31 | 89.85 | 83.94 ± 11.84 | 31.75 | 8.50 | 29.38 | 23.21 ± 12.79 |
| 20 | 96.87 | 95.08 | 93.10 | 95.02 ± 1.89 | 7.69 | 29.71 | 30.91 | 22.77 ± 13.07 |
| 30 | 95.94 | 88.63 | 87.77 | 90.78 ± 4.49 | 37.94 | 27.83 | 41.78 | 35.85 ± 7.21 |
| 40 | 96.80 | 95.47 | 95.33 | 95.87 ± 0.81 | 23.50 | 30.08 | 48.04 | 38.87 ± 12.70 |
| 50 | 95.73 | 93.25 | 95.38 | 94.79 ± 1.34 | 33.36 | 41.45 | 45.66 | 40.16 ± 6.25 |

The results presented in 1.1-1.3 illustrate that $ApoE_{141\text{-}149dp}$ was more efficacious than $ApoE_{263\text{-}286}$. In the light of these results, the inventors proceeded to test other peptides generated from apolipoproteins to investigate whether or not such peptides had antiviral activity (see Example 2).

EXAMPLE 2

Given the knowledge gained by the inventors following the work reported in Example 1, experiments were conducted to evaluate the antiviral effects of a large number of peptides derived from apoB and other apolipoproteins. Regions tested included heparin binding regions, the LDLR binding region or apolipoprotein B, and amphipathic alpha helical regions. Where peptides were short, tandem repeats were constructed to increase likelihood of alpha helix formation.

Surprisingly, the inventors found that only a minority of the peptides derived from other apolipoproteins had antiviral effects (see 2.2). Such peptides represent peptides according to the invention.

2.1 Materials and Methods 2.1.1 Cell Culture

African Green Monkey Kidney (Vero) cells were maintained in Eagle's minimum essential medium with Earle's salt (EMEM) and supplemented with 10% foetal calf serum (heat-inactivated), 4 mM L-glutamine, and 1% (v/v) nonessential amino acids, plus penicillin and streptomycin (100 IU/ml and 100 μg/ml, respectively) (maintenance medium referred to as 10% EMEM). The cells were incubated at 37° C. in a humidified atmosphere of air with 5% $CO_2$.

On harvesting, monolayers were washed in phosphate-buffered saline (PBS), and dislodged by incubating with trypsin in PBS for 30 min, before inactivating trypsin by addition of an equal volume of 10% EMEM and centrifuging at 500 g (5 min, 4° C.). Cell pellets were resuspended in 10% EMEM, prior to cell counting and seeding of 24-well plates. For antiviral assays, medium containing only 0.5% FCS was used (referred to as 0.5% EMEM).

2.1.2 Virus

Three separate passages of HSV1 virus were prepared by infecting Vero cells, and preparing semi-pure suspensions of virus from tissue culture supernatant and cell lysates, before freezing aliquots of virus at −85° C. Viral infectivity was assessed by carrying out plaque assays on serial dilutions of thawed aliquots (expressed in pfu/ml).

2.1.3 Peptides

Peptides were obtained in lyophilised form from a commercial supplier (AltaBioscience, University of Birmingham or Advanced Biomedical), and were produced at 5 micromole scale. N-terminals were protected by addition of an acetyl group, and the C-terminals were protected by addition of an amide group.

Figure 7:
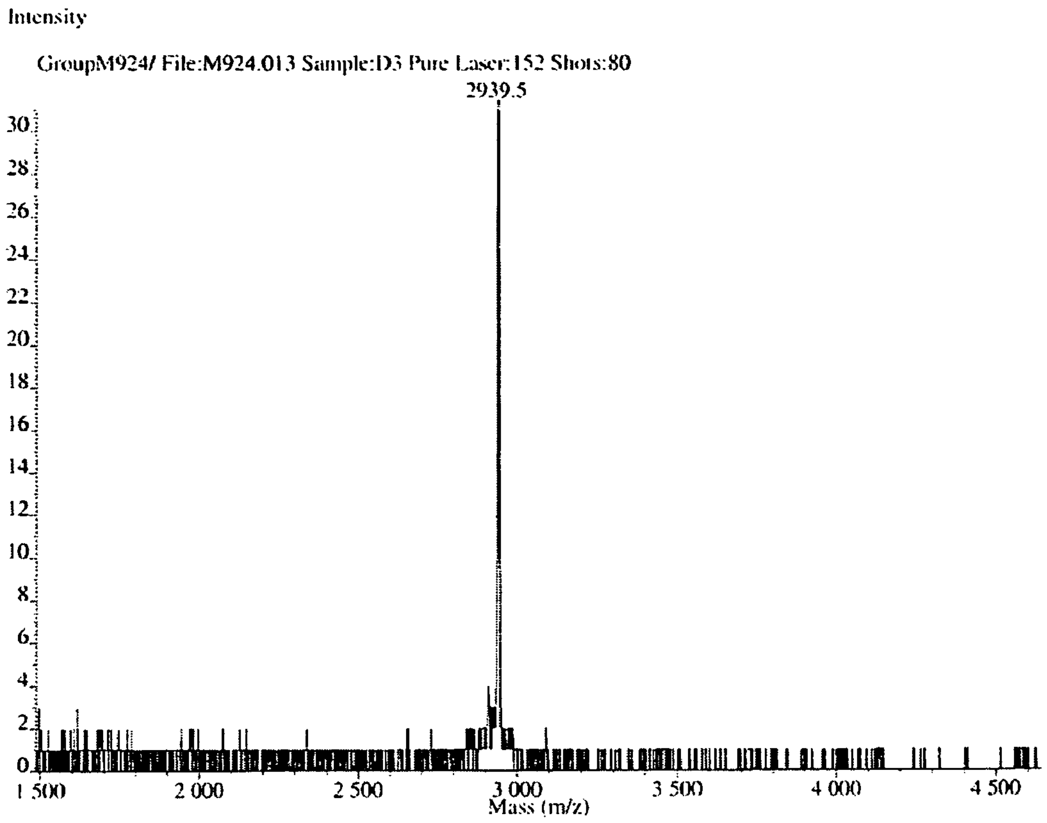
FIG. 7 shows typical mass spectrometry data for MU 27 (the expected mass ion value was 2939.5, which exactly matches the value obtained)
Figure 8:
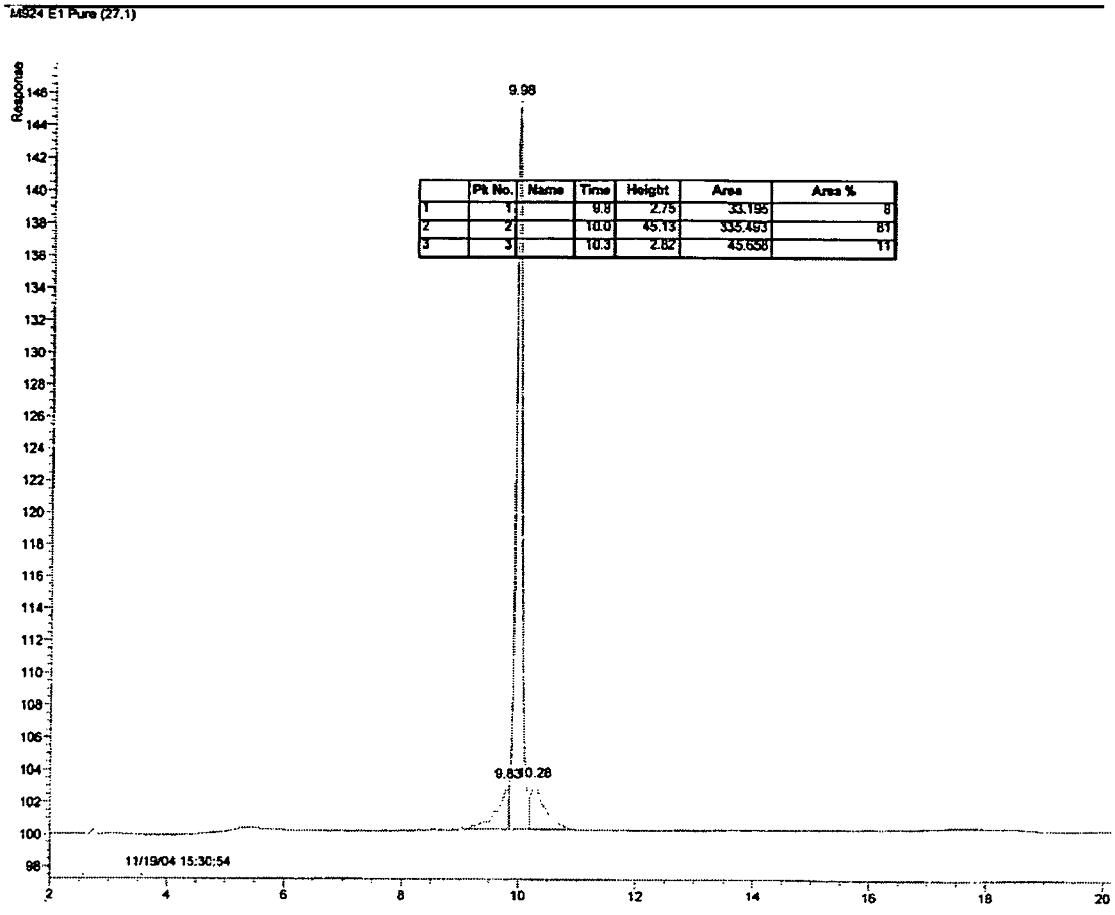
FIG. 8 shows typical HPLC purification data for MU 27 and illustrates that the peptide generally >80% purity.

Molecular weight of peptides was confirmed by laser desorption mass spectrometry using a Finnigan LASERMAT 2000 MALDI-time of flight mass analyzer or a Scientific Analysis Group MALDI-TOF mass spectrometer. HPLC purification of peptides was performed using a Vydac analytical C-4 reverse phase column, using 0.1% TFA and 0.1% TFA/80% acetonitrile as solvents, or for some peptides an ACE C18 Reverse Phase column, using 0.05% TFA and 60% acetonitrile as solvents. Typical mass spectrometry data and high performance liquid chromatography (HPLC) traces (purity >80%) for peptide MU 27 (SEQ ID No. 3) are shown in FIGS. 7 and 8.

Small quantities of peptide were weighed in sterile Eppendorf tubes, before addition of sufficient 0.5% EMEM to produce a 1.5 mM stock solution, which was frozen at −20° C. in aliquots.

2.1.4 Plaque Reduction Assays

Vero cells were seeded at 125,000 cells per well in 10% EMEM, and were incubated overnight resulting in confluent monolayers. Peptides were diluted in 0.5% EMEM to give 2× final desired concentration, and 100 μl aliquots were arranged on 96-well plates in arrangement to be used for 24-well plate; control wells containing normal 0.5% EMEM were also prepared. Virus stocks (p3) were thawed, and diluted in 0.5% EMEM such that there were around 100 pfu in 100 μl. Each 24-well plate was inoculated separately. Firstly 100 μl of virus stock was added to the peptide or control medium arranged on a 96-well plate. This was incubated at 37° C. for ten minutes before inoculation. Medium was removed from four wells of a 24-well plate containing confluent Vero, and the 200 μl inoculum added to the appropriate well. Once all wells were treated, the 24-well plate was incubated for a further 60-80 minutes. Finally the peptide-containing inoculum was removed, and 1 ml of 1% EMEM containing 1% carboxymethylcellulose was added to each well. Plates were incubated for a further 22 hours, before removal of overlay, and addition of 10% formaldehyde in PBS. After a further one hour incubation, fixative was removed, monolayers washed several times with tap water, and stained with carbol fuchsin solubilised in water. After 30 minutes stain was removed, and plates washed several times with tap water, before being air dried. Plaques were counted using an Olympus IX70 Inverting Microscope, and antiviral effect expressed as a percentage of the control value for each peptide concentration. The IC50 was calculated from plots of inhibitory effect against peptide concentration.

2.1.5 Toxicity Testing

Vero cells were seeded in 96-well plates at 30,000 cells per well in 10% EMEM, and were incubated overnight resulting in confluent monolayers. GIN peptides were diluted in 0.5% EMEM to give final desired concentration, and 100 μl aliquots were arranged on separate non-cell containing 96-well plates, prior to taking Vero 96-well plates, removing 10% EMEM, and adding 0.5% EMEM containing peptides. After incubating for 48 hours, 25 μl of 1.5 mg/ml MTT solution (in 0.5% EMEM) was added per well, and plates returned to incubator for one hour. Finally, medium was removed from wells, and blue formazan crystals solubilised by addition of 100 µl of dimethylsulphoxide (DMSO). Absorbance of resulting solutions was then measured at 570 nm, and toxic effect expressed as a percentage of the control value for each peptide concentration. Where possible, the EC50 was calculated from plots of toxic effect against peptide concentration. Fortunately, no evidence of toxicity was found for the cell line tested, using peptide at 40 µM exposed to cells for 2 days.

2.2 Results

Figure 4:
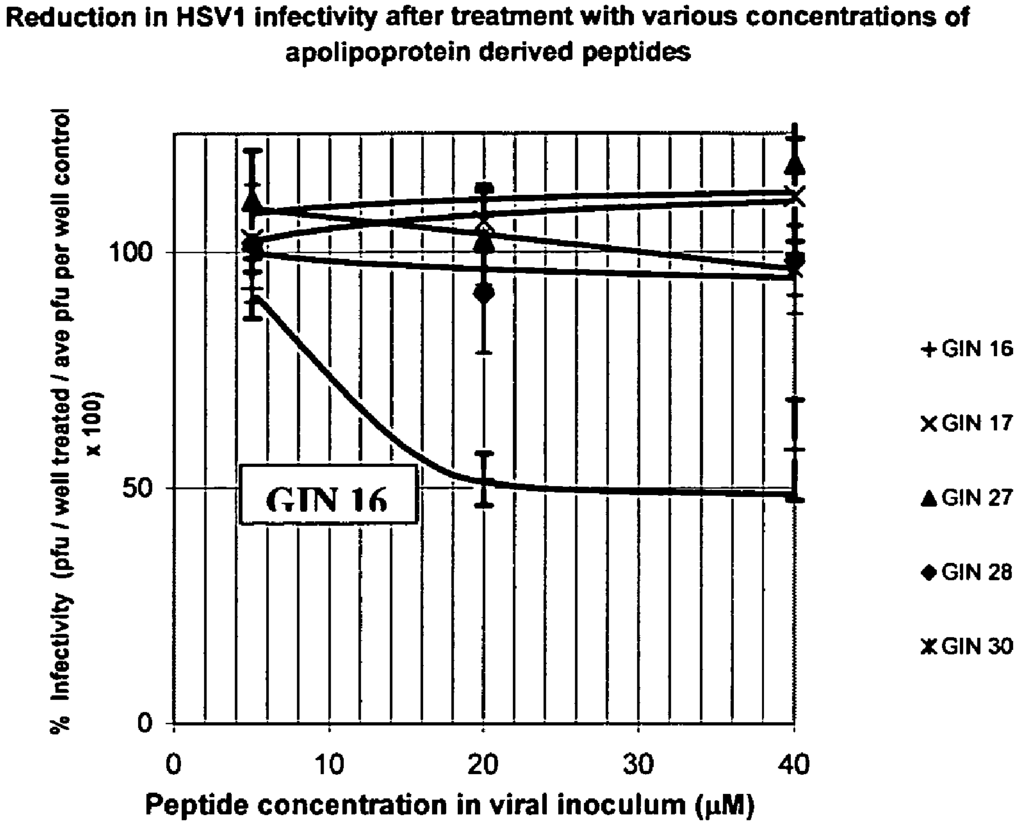
FIG. 4 illustrates the effect of five peptides (GIN 16, GIN 17, GIN 27, GIN 28, and GIN 30) on HSV1 infectivity as described in Example 2.

FIG. 4 illustrates data obtained for five peptides identified as GIN 16 (SEQ ID No. 48), GIN 17 (SEQ ID No.15), GIN 27 (SEQ ID No.16), GIN 28 (SEQ ID No.17), and GIN 30 (SEQ ID No.18). FIG. 4 clearly shows that surprisingly only GIN 16 according to the first aspect showed antiviral activity, whereas GIN 17, GIN 27, GIN 28 and GIN 30 did not.

Table 4 below summarises data obtained for GIN peptides constructed from a range of human apolipoproteins.

TABLE 4

Data obtained for GIN peptides constructed from a range of human apolipoproteins against HSV1.

| Peptide | Sequence | Source of peptide | IC50 (µM) |
|---|---|---|---|
| GIN 16 | LRTRKRGRKLRTRKRGRK (SEQ ID No. 48) | Human apolipoprotein $B_{(3359-3367)\,repeat}$ in which residues 3359 and 3360 reversed, and leucine residue at position 3366 replaced with an arginine. | 22 |
| Sequences where activity low: | | | |
| GIN 22 | DWLKAFYDKVAEKLKEAF (SEQ ID No. 20) | Amphipathic alpha helical peptide with antiviral properties (derived from apolipoprotein A1 by Ananatharamiash supra and tested against HIV by Srinivas supra (also known as peptide 18A) | 36 |
| GIN 29 | HMLDVMQDHFSRASSIIDEL (SEQ ID No. 21) | Amphipathic alpha helical region of human apolipoprotein J (apoJ 171-190) | 38.5 |
| GIN 13 | RDADDLQKR RDADDLQKR (SEQ ID No. 22) | Tandem repeat peptide derived from one section of primary human apoE heparin binding region (apoE $_{(150-158)\,repeat}$) | >40 |
| GIN 14 | GERLRARMEGERLRARME (SEQ ID No. 19) | Tandem repeat derived from second human apoE heparin binding $region_{(211-219)\,repeat}$ | >40 |
| GIN 15 | RLRARMEEMRLRARMEEM (SEQ ID No. 23) | Tandem repeat derived from second human apoE heparin binding $region_{(213-221)\,repeat}$ | >40 |
| Sequences where activity not detectible | | | |
| apoE 141-149 | LRKLRKRLL (SEQ ID No. 24) | Human apoE LDLR/ heparin binding region. | NA |
| GIN 17 | RALVDTLKFVTQAEGAK (SEQ ID No. 15) | Human apoB heparin binding region. | NA |
| GIN 18 | PYLDDFQKKWQEEMELYRQKVE (SEQ ID No. 25) | Human apoA1 helical domain 4 | NA |
| GIN 19 | PLGEEMRDRARAHVDALRTHLA (SEQ ID No. 26) | Human apoA1 helical domain 6 | NA |
| GIN 20 | PYSDELRQRLAARLEALKENGG (SEQ ID No. 27) | Human apoA1 helical domain 7 | NA |
| GIN 21 | ARLAEYHAKATEHLSTLSEKAK (SEQ ID No. 28) | Human apoA1 helical domain 8 | NA |
| GIN 23 | PVLDEFREKLNEELEALKQKMK (SEQ ID No. 29) | Consensus domain from human apoA1 (Ananatharamiah supra) | NA |
| GIN 24 | VTDYGKDLMEKVKSPELQ (SEQ ID No. 30) | Human apolipoprotein AII amphipathic alpha helical region (residues 18-35) | NA |
| GIN 25 | VTDYGKDLMEKVKEWLNS (SEQ ID No. 31) | Human apolipoprotein AII amphipathic alpha helical region (residues 18-35) +modification by Bucko et al., bit J Pept Protein Res. 1996; 48:21-30 | NA |
| GIN 26 | NFHAMFQPFLEMIHEAQQ (SEQ ID No. 32) | Human apolipoprotein J amphipathic helix 3 (Bailey et al. supra) | NA |
| GIN 27 | CKNKEKKCCKNKEKKC (SEQ ID No. 16) | Human apolipoprotein H heparin binding region (tandem repeat) $ApoH_{(281-288)\,repeat}$ | NA |
| GIN 28 | LRKEKKRLLLRKEKKRLL (SEQ ID No. 17) | Modification of GIN 27 | NA |

TABLE 4-continued

Data obtained for GIN peptides constructed from a range of human apolipoproteins against HSV1.

| Peptide | Sequence | Source of peptide | IC50 (μM) |
|---|---|---|---|
| GIN 30 | LQVAERLTRKYNELLKSYQ (SEQ ID No. 18) | Human apolipoprotein J amphipathic helix 4 (Bailey et al. 2001) | NA |
| GIN 31 | KFMETVAEKALQEYRK (SEQ ID No. 33) | Human apolipoprotein I amphipathic helix 5 (Bailey et al. 2001) | NA |

EXAMPLE 3

Figure 5:
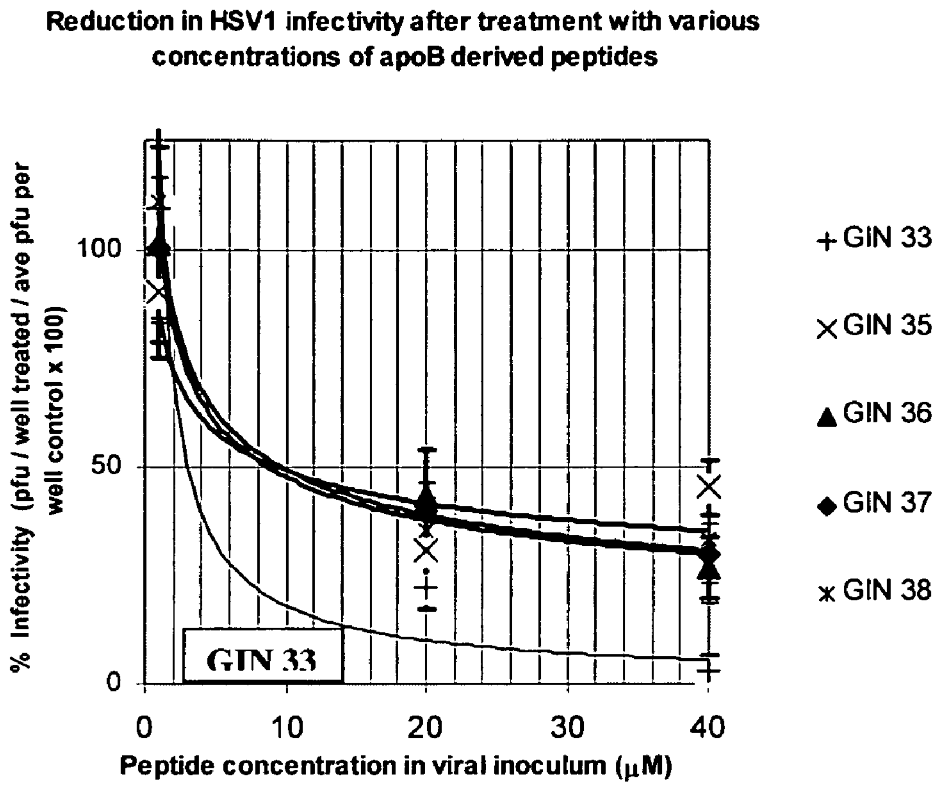
FIG. 5 illustrates the effect of five peptides (GIN 33, GIN 35, GIN 36, GIN 37, and GIN 38) on HSV1 infectivity as described in Example 2.

A further set of experiments were conducted on expanded number of peptides to further evaluate the effect of peptides according to the invention against HSV-1. Table 5 below and FIG. 5 confirms that the peptides designated GIN 33 (SEQ ID No.7), GIN 35 (SEQ ID No.3), GIN 36 (SEQ ID No.4), GIN 37 (SEQ ID No.5), and GIN 38 (SEQ ID No.6) according to the first aspect of the present invention have antiviral activity.

TABLE 5 summarises anti-HSV1 ata obtained for GIN peptides derived from GIN 16

| Peptide | SEQ ID No. | Sequence | IC50 (μM) |
|---|---|---|---|
| GIN 33 | 7 | WRWRKRWRKWRWRKRWRK | 3 |
| GIN 35 | 3 | RTRKRGRKRTRKRGRK | 9 |
| GIN 36 | 4 | RTRKRGRRTRKRGR | 9 |
| GIN 37 | 5 | LRKRKRLLRKRKRL | 9 |
| GIN 38 | 6 | LRKRKRLRKLRKRKRLRK | 9 |

EXAMPLE 4

Similar experiments to those described in Example 2 were conducted to test the efficacy of the peptides according to the invention against HIV infection. The glioma cell line NP2 over-expressing both CD4 and the appropriate co-receptor (CCR5 or CXCR4) were maintained in DMEM supplemented with 10% FCS. $2\times10^4$ cells were plated per well of a 48-well plate 24 h prior to infection and grown at 37 C. The cells were then washed, and incubated in DMEM/FCS containing peptide concentrations ranging from 0.1 to 10 micromolar, at 37 C for 30 minutes. 200 focus-forming units of HIV-1 stocks were then added to each well, and the cells incubated at 37 C for a further 2 hours. The cells were then washed twice in PBS and fresh medium replaced. After 3 day's growth the cells were fixed in cold methanol:acetone, and stained in situ for expression of HIV-1 p24 using a monoclonal anti-p24 followed by a secondary anti-mouse beta-galactosidase conjugate. Expression was visualised by X-Gal staining and infectious foci enumerated by light-microscopy.

Figure 6:
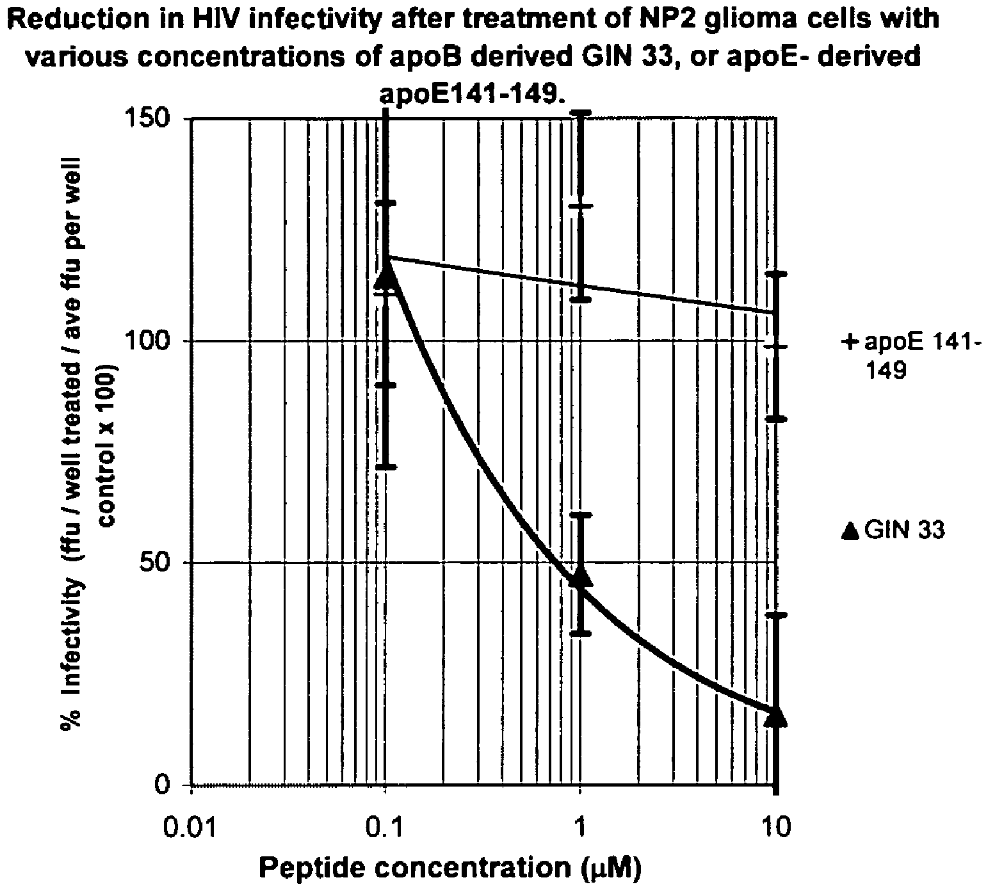
FIG. 6 illustrates the anti-HIV action of peptide GIN33 against HIV isolate SF162, grown in NP-2 glioma cells over-expressing CCR5 co-receptors as described in Example 4.

It was found that peptides according to the invention had similar efficacy against HSV-1 and HIV. FIG. 6 illustrates the anti-HIV action of peptide GIN 33 (SEQ ID No.7) against HIV isolate SF162, grown in NP-2 glioma cells overexpressing CCR5 co-receptors.

EXAMPLE 5

Further experiments were conducted to test the efficacy of peptides according to the present invention against HSV1.

5.1 Methods

The methods employed were as described in Examples 1-4 expect peptides were prepared as 400 μM stocks in phosphate buffered saline (PBS).

5.2 Results 5.2.1 Effect of Further ApoB Peptides According to the Present Invention

TABLE 6

| Peptide Code | SEQ ID No. | Sequence | HSV1 IC50 (μM) |
|---|---|---|---|
| MU_27 (GIN 33) | 7 | WRWRKRWRKWRWRKRWRK | 14 |
| MU_28 | 34 | RRWRKRWRKWRWRKRWRK | 7.5 |
| MU_29 | 35 | KRWRKRWRKWRWRKRWRK | 7.5 |
| MU_30 | 36 | LRWRKRWRKWRWRKRWRK | 7.5 |
| MU_31 | 37 | HRWRKRWRKWRWRKRWRK | 7.5 |
| MU_32 | 38 | RWRKRWRKWRWRKRWRK | 7.5 |
| MU_33 | 39 | RRWRKRWRKRRWRKRWRK | 6.5 |
| MU_34 | 40 | KRWRKRWRKKRWRKRWRK | 9 |
| MU_35 | 41 | LRWRKRWRKLRWRKRWRK | >15 |
| MU_36 | 42 | HRWRKRWRKHRWRKRWRK | 10 |
| MU_37 | 43 | RWRKRWRKRWRKRWRK | 12.5 |
| MU_69 | 44 | RWRKRGRKRWRKRGRK | 13 |
| MU_70 | 45 | RTRKRWRKRTRKRGRK | 9.5 |
| MU_71 | 46 | RWRKRWRKRWRKRWRK | 16 |
| MU_84 | 47 | RWRKRWRWRKRWRWRKRW | 10 |

MU 35 was found to be active against HSV-1. However HSV activity was not reduced by 50% at concentrations up to 15 μM.

EXAMPLE 6

Further experiments were conducted to test the efficacy of peptides according to the present invention against HSV2.

6.1 Methods

Plaque assays were performed. The methodology was as described in previous Examples for HSV1 plaque assays (including usage of Vero cells) except HSV2 clinical isolates (provided by Prof. Anthony Hart of Liverpool University) were employed instead.

6.2 Results

A number of peptides that were found to have efficacy against HSV1 were also tested against HSV2. Table 7 illustrates that peptides according to the present invention were effective against both HSV1 and HSV2. This illustrates that the peptides will have broad spectrum activity against viruses.

TABLE 7

| Peptide Code | SEQ ID No. | Sequence | HSV2 IC50 (μM) |
|---|---|---|---|
| MU_27 (GIN 33) | 7 | WRWRKRWRKWRWRKRWRK | 10 |
| MU_32 | 38 | RWRKRWRKWRWRKRWRK | >20 |
| MU_33 | 39 | RRWRKRWRKRRWRKRWRK | >20 |
| MU_70 | 45 | RTRKRWRKRTRKRGRK | >20 |

MU 32, 33 and 70 were found to be active against HSV-2. However HSV-2 activity was not reduced by 50% at concentrations up to 20 μM.

EXAMPLE 7

Further experiments were conducted to test the efficacy of peptides according to the present invention against Human Immunodeficiency Virus (HIV). The effect of a peptide according to the present invention was test against a different HIV strain to that tested in Example 4.

7.1 Methods

Peptides (prepared as described previously) were diluted in 50 μl aliquots and mixed with T-cells (C8166) at 40,000 cells per well. Next HIV-1 111B was added at a multiplicity of infection (MOI) of 0.01, and the mixture incubated for 5 days at 37° C. Syncytia formation was assessed visually using an inverting microscope, and viral gp120 levels in supernatants assessed by a gp120 ELISA using GNA for antigen capture. 96-well plates coated with 50 ul GNA (Galanthus nivalis) were washed, then treated with 100 μl RPMI (10% foetal calf serum) and left for one hour. After further washing, 25 μl test sample supernatants were added to wells, along with dilutions of infected control samples. After lysis by 3 hr treatment with 0.5% Empigen (detergent used to lyse virus) to all wells, and washing, 50 μl of human anti-HIV sera was added, and plates incubated overnight. After further washing, 50 μl of a 1000× dilution of anti-human Ig peroxidase conjugate was added, and plates incubated at 37° C. for 90 min. After a final wash, 50 ul peroxidase substrate was added to each well, and plates incubated for 10-30 min. Reaction was stopped with 25 μl 2M $H_2SO_4$, and A450 measured.

7.2 Results

Further tests were conducted to support the data presented in Example 4 illustrating that peptides according to the present invention were effective against HIV as well as both HSV1 and HSV2.

TABLE 8

| Peptide Code | SEQ ID No. | Sequence | HIV IC50 (μM) |
|---|---|---|---|
| MU_32 | 38 | RWRKRWRKWRWRKRWRK | 4.65 |
| MU_33 | 39 | RRWRKRWRKRRWRKRWRK | 5.15 |

The invention claimed is:

1. An isolated polypeptide or analogue thereof, comprising a tandem repeat of apolipoprotein B, wherein the isolated polypeptide or analogue thereof is according to formula I:

abcRKRxyza'b'c'RKRx'y'z' (I)

wherein a and a' are each independently selected from the group consisting of a positively charged residue, which is Arginine (R), Lysine (K) or Histidine (H), Leucine (L), Tryptophan (W), and deleted;

b and b' are each independently selected from the group consisting of Leucine (L), Arginine (R), Lysine (K), and deleted;

c and c' are each independently selected from the group consisting of Threonine (T), Tryptophan (W), and a positively charged residue, which is Arginine (R), Lysine (K) or Histidine (H);

x and x' are each independently selected from the group consisting of Glycine (G), Tryptophan (W), Leucine (L), and a positively charged residue, which is Arginine (R), Lysine (K) or Histidine (H);

y and y' are each independently selected from the group consisting of Leucine (L), a positively charged residue, which is Arginine (R), Lysine (K) or Histidine (H), and deleted; and z and z' are each independently selected from the group consisting of a positively charged residue, which is Arginine (R), Lysine (K) or Histidine (H), Leucine, and deleted, or a truncation thereof comprising the tandem repeat of apolipoprotein B, characterized in that the tandem repeat or truncation thereof comprising the tandem repeat of apolipoprotein B is obtained from a heparin sulphate proteoglycan (HSPG) receptor binding region of apolipoprotein B.

2. The isolated polypeptide or analogue thereof according to claim 1, wherein the polypeptide or analogue thereof comprises a tandemmrepeat which is obtained from an apolipoprotein B low density lipoprotein (LDL) receptor binding domain cluster B.

3. The isolated polypeptide or analogue thereof according to claim 1 comprising a tandem repeat of human apolipoprotein $B_{(3359-3367)}$ having amino acid sequence RLTRKRGLK (SEQ ID NO:1), or a truncation thereof comprising the tandem repeat.

4. The isolated polypeptide or analogue thereof according to claim 3, wherein at least one of the first, second, third, seventh, eighth, ninth, tenth, eleventh, twelfth, sixteenth, seventeenth or eighteenth residues is further substituted or deleted.

5. The isolated polypeptide or analogue thereof according to claim 1 comprising a tandem repeat of the amino acid sequence of SEQ ID NO:1.

6. The isolated polypeptide or analogue thereof according to claim 5, wherein at least one of the first, second, third, seventh, eighth, ninth, tenth, eleventh, twelfth, sixteenth, seventeenth or eighteenth residues is further substituted or deleted.

7. The isolated polypeptide or analogue thereof according to claim 1 consisting of the amino acid sequence:

LRTRKRGRKLRTRKRGRK (SEQ ID NO:48);
RTRKRGRKRTRKRGRK (SEQ ID NO:3);
RTRKRGRRTRKRGR (SEQ ID NO:4);
LRKRKRLLRKRKRL (SEQ ID NO:5);
LRKRKRLRKLRKRKRLRK (SEQ ID NO:6);
WRWRKRWRKWRWRKRWRK (SEQ ID NO:7);
RRWRKRWRKWRWRKRWRK (SEQ ID NO:34);
KRWRKRWRKWRWRKRWRK (SEQ ID NO:35);
LRWRKRWRKWRWRKRWRK (SEQ ID NO:36);
HRWRKRWRKWRWRKRWRK (SEQ ID NO:37);
RWRKRWRKWRWRKRWRK (SEQ ID NO:38);
RRWRKRWRKRRWRKRWRK (SEQ ID NO:39);
KRWRKRWRKKRWRKRWRK (SEQ ID NO:40);
LRWRKRWRKLRWRKRWRK (SEQ ID NO:41);
HRWRKRWRKHRWRKRWRK (SEQ ID NO:42);
RWRKRWRKRWRKRWRK (SEQ ID NO:43);
RWRKRGRKRWRKRGRK (SEQ ID NO:44);
RTRKRWRKRTRKRGRK (SEQ ID NO:45);
RWRKRWRKRWRKRWRK (SEQ ID NO:46); or
RWRKRWRWRKRWRWRKRW (SEQ ID NO:47).

8. A composition, comprising the isolated polypeptide or analogue thereof according to claim 1.

9. A method of treating a viral infection, comprising administering to a subject in need of treatment a therapeutically effective amount of the polypeptide or analogue according to claim 1.

* * * * *